United States Patent [19]

Maruo et al.

[11] Patent Number: 6,016,435
[45] Date of Patent: Jan. 18, 2000

[54] DEVICE FOR NON-INVASIVE DETERMINATION OF A GLUCOSE CONCENTRATION IN THE BLOOD OF A SUBJECT

[75] Inventors: Katsuhiko Maruo, Itami; Keisuke Shimizu, Neyagawa; Masami Oka, Osaka, all of Japan

[73] Assignee: Matsushita Electric Works Ltd., Osaka, Japan

[21] Appl. No.: 08/978,266

[22] Filed: Nov. 25, 1997

[30] Foreign Application Priority Data

Nov. 26, 1996 [JP] Japan ..................... 8-314379
Jun. 25, 1997 [JP] Japan ..................... 9-169267
Oct. 3, 1997 [JP] Japan ..................... 9-271709

[51] Int. Cl.⁷ ....................................... A61B 5/00
[52] U.S. Cl. ............................. 600/316; 600/473
[58] Field of Search ..................... 600/310, 316, 600/322, 326, 473, 476; 250/339.11, 339.12; 356/39

[56] References Cited

U.S. PATENT DOCUMENTS

| | | | |
|---|---|---|---|
| 4,655,225 | 4/1987 | Dähne et al. | 600/316 |
| 5,070,874 | 12/1991 | Barnes et al. | |
| 5,086,229 | 2/1992 | Rosenthal et al. | |
| 5,333,610 | 8/1994 | Hirao | 128/633 |
| 5,379,764 | 1/1995 | Barnes et al. | 128/633 |
| 5,434,412 | 7/1995 | Sodickson et al. | |
| 5,551,422 | 9/1996 | Simonsen et al. | 128/633 |

FOREIGN PATENT DOCUMENTS 0 757 243 A1  2/1997  European Pat. Off. .
29 34 190 A1  3/1981  Germany .

*Primary Examiner*—Eric F. Winakur
*Attorney, Agent, or Firm*—Armstrong, Westerman Hattori, McLeland & Naughton

[57] ABSTRACT

A device for non-invasive determination of a glucose concentration in the blood of a subject which includes a light source for producing near-infrared radiation having successive wavelengths within a range of 1300 nm to 2500 nm, a light projecting unit for projecting the near-infrared radiation on a skin of the subject, a light receiving unit for receiving a resulting radiation emitted from the inside of the skin, and a spectrum analyzing unit for making a spectrum analysis of the resulting radiation, and determining the glucose concentration according to the spectrum analysis. The light receiving unit is separated from the light projecting unit by a distance defined within a range of 0.1 mm to 2 mm to selectively sense the resulting radiation emitted from a dermis layer positioned under an epidermis layer of the skin. The glucose concentration in the blood is determined at the spectrum analyzing unit by using the spectrum analysis and a statistically-obtained correlation between glucose concentration in dermis region and glucose concentration in blood of test subjects.

22 Claims, 31 Drawing Sheets

DEVICE FOR NON-INVASIVE DETERMINATION OF A GLUCOSE CONCENTRATION IN THE BLOOD OF A SUBJECT

BACKGROUND OF THE INVENTION

1. Field of the Invention

The present invention relates to a device for non-invasive determination of a glucose concentration in the blood of a subject with improved accuracy.

2. Disclosure of the Related Art

In the past, a near-infrared spectroscopic analysis has been known as a method comprising the steps of projecting near-infrared radiation having wavelengths of 800 nm to 2500 nm to a target, receiving a resulting radiation, i.e., a transmission light or reflection light from the target, and performing a spectrum analysis of the resulting radiation. This method has the following advantages:

(1) Since a low energy electromagnetic wave is used, it is possible to avoid the occurrence of radiation damage of the target.

(2) An absorption by water of near-infrared radiation is smaller than that of infrared radiation, therefore, it is possible to select an aqueous solution as the target.

(3) It is possible to perform the spectroscopic analysis under various physical states of the target, i.e., a solid state such as powder or fiber, a liquid state and a gas state.

As an application of the near-infrared spectroscopic analysis, it is increasingly utilized for non-invasive determination of a glucose concentration in the body of a subject. For example, U.S. Pat. No. 5,379,764 discloses a method of determining a glucose concentration in the blood of a patient. FIG. 39 is a schematic diagram of a device for practicing the method. Near-infrared radiation is provided from a light source 1Y which is capable of producing the radiation over the range of 700 nm to 3000 nm, and projected on a skin 9Y of the patient through a first lens system 2Y and an input radiation conductor 10Y, e.g., optical fibers. A resulting back-scattered radiation emitted from the inside of the skin 9Y is received by a sensing radiation conductor 20Y. The received radiation is provided through a second lens system 3Y to a spectrum analyzer/detector 30Y, and then a data processor 40Y to make a spectrum analysis of the received radiation and determine the glucose concentration in the blood of the patient by using a multivariate analysis. The obtained glucose concentration is sent to a display monitor 50Y and an output recorder 60Y.

On the other hand, PCT Publication No. WO94/10901 discloses a method for determining a glucose concentration in a biological matrix. As shown in FIG. 40, the method uses a light emitter (not shown) for projecting a primary light 1Z of near-infrared radiation at a projection site 10Z to a skin 9Z of the biological matrix, and first and second light receivers (not shown) for sensing resulting secondary lights (2Z, 3Z) emitted from the skin 9Z at first and second detection sites (20Z, 30Z). The first detection site 20Z is spaced from the projection site 10Z by a distance D1 of at least 0.5 mm, and preferably 1 mm. The second detection site 30Z is spaced from the projection site 10Z by a distance D2 (#D1) of 30 mm or less. A light path passing through the skin 9Z between the projection site 10Z and the first detection site 20Z is different from the light path passing through the skin between the projection site and the second detection site 30Z. Therefore, the glucose concentration can be derived from the dependence of the intensity of the secondary light from the relative position of the projection site and the detection site.

By the way, each of these measurements of the glucose concentration is performed by projecting near-infrared radiation on a skin of a forearm or finger of the subject. The skin is generally composed of three layers, that is, an epidermis layer having a thickness of about 100 μm, a dermis layer having a thickness of about 1 mm and positioned under the epidermis layer, and a subcutaneous-tissue layer including adipose cells and positioned under the dermis layer. These layers shows different glucose concentrations. Therefore, if variations in glucose concentration on such a complex skin structure is carefully analyzed, it will be possible to determine the glucose concentration in the blood with improved accuracy. Thus, there is room for further improvement on the measurements of the glucose concentration of the prior art.

SUMMARY OF THE INVENTION

A primary object of the present invention is to provide a device for non-invasive determination of a glucose concentration in the blood of a subject with improved accuracy. The device comprises a light source for producing near-infrared radiation having successive wavelengths within a range of 1300 nm to 2500 nm, a light projecting unit for projecting the near-infrared radiation on a skin of the subject, light receiving unit for receiving a resulting radiation emitted from the inside of the skin, and a spectrum analyzing unit for making a spectrum analysis of the resulting radiation and determining the glucose concentration in the blood according to the spectrum analysis. The light receiving unit is separated from the light projecting unit by a distance defined within a range of 0.1 mm to 2 mm to selectively receive the resulting radiation emitted from a dermis layer positioned under an epidermis layer of the skin. The glucose concentration in the blood of the subject is determined in the spectrum analyzing unit by using the spectrum analysis and a statistically-obtained correlation between glucose concentration in dermis layer and glucose concentration in blood of test subjects. Due to a relatively uniform glucose concentration in the dermis layer, it is possible to reliably provide the glucose concentration in the blood of the subject with improved accuracy.

It is preferred that the light projecting unit is formed with a plurality of first optical fibers each of which is connected at its one end to the light source, and provides the near-infrared radiation from its opposite projection end, and that the light receiving unit is formed with a plurality of second optical fibers each of which is connected at its one end to the spectrum analyzing unit, and receives the resulting radiation at its opposite receiving end. In particular, it is preferred that the first optical fibers make a bundle in cooperation with the second optical fibers, and projection ends of the first optical fibers and receiving ends of the second optical fibers are exposed at an end surface of the bundle in such a pattern that a center of each of the projection ends is separated from a center of an adjacent receiving end by a distance defined within the range of 0.1 mm to 2 mm, and more preferably 0.2 mm to 1 mm.

In a preferred embodiment of the present invention, the center of each of the projection ends is at least spaced from the center of the adjacent receiving end by a distance L expressed by the following equation;

$$L = \{\sqrt{2} \times (d1 + d2)\}/2$$

wherein d1 is a diameter of the first optical fiber, and d2 is a diameter of the second optical fiber. When the first and second optical fibers have a same diameter d, the distance L is expressed by the equation;

$$L = \sqrt{2} \times d.$$

In a further preferred embodiment of the present invention, the bundle is formed with a plurality of sub-bundles, in each of which a projection end of the first optical fiber is disposed on the end surface of the bundle at a center of a hexagonal pattern, and six receiving ends of the second optical fibers are disposed at corners of the hexagonal pattern. In this case, it is preferred that at least one of the receiving ends of each of the sub-bundles is common with an adjacent sub-bundle. This provides an advantage of uniformly detecting the resulting radiation selectively including spectrum information of the dermis layer from a relatively wide area of the skin. Therefore, the reliability of measurement of the glucose concentration could be improved.

In another preferred embodiment of the present invention, the device comprises a supplemental light receiving unit which is formed with plurality of third optical fibers. Each of the third optical fibers is connected at its one end to the spectrum analyzing unit, and selectively receives at its opposite receiving end the resulting radiation emitted from the epidermis layer. The receiving end of each of the third optical fibers is disposed on the end surface of the bundle between the projection end and one of the receiving ends in the respective hexagonal pattern. As explained before, the resulting radiation received by the second optical fibers selectively contains the spectrum information of the dermis layer, however, a small amount of spectrum information of the epidermis layer is inevitably included in the resulting radiation. The supplemental light receiving unit is preferably used to subtract the spectrum information of the epidermis layer from the resulting radiation received by the second optical fibers. As a result, it is possible to achieve the spectrum analysis of the resulting radiation, while minimizing the influence of undesirable spectrum information from the epidermis layer.

These and still other objects and advantages will become apparent from the following description of the preferred embodiments of the invention when taken in conjunction with the attached drawings.

BRIEF DESCRIPTION OF THE DRAWINGS

In FIGS. 6A to 6C, FIGS. 6A and 6B show a method of forming the optical fiber bundle;

DETAIL DESCRIPTION OF THE PREFERRED EMBODIMENTS

First Embodiment

Figure 1:
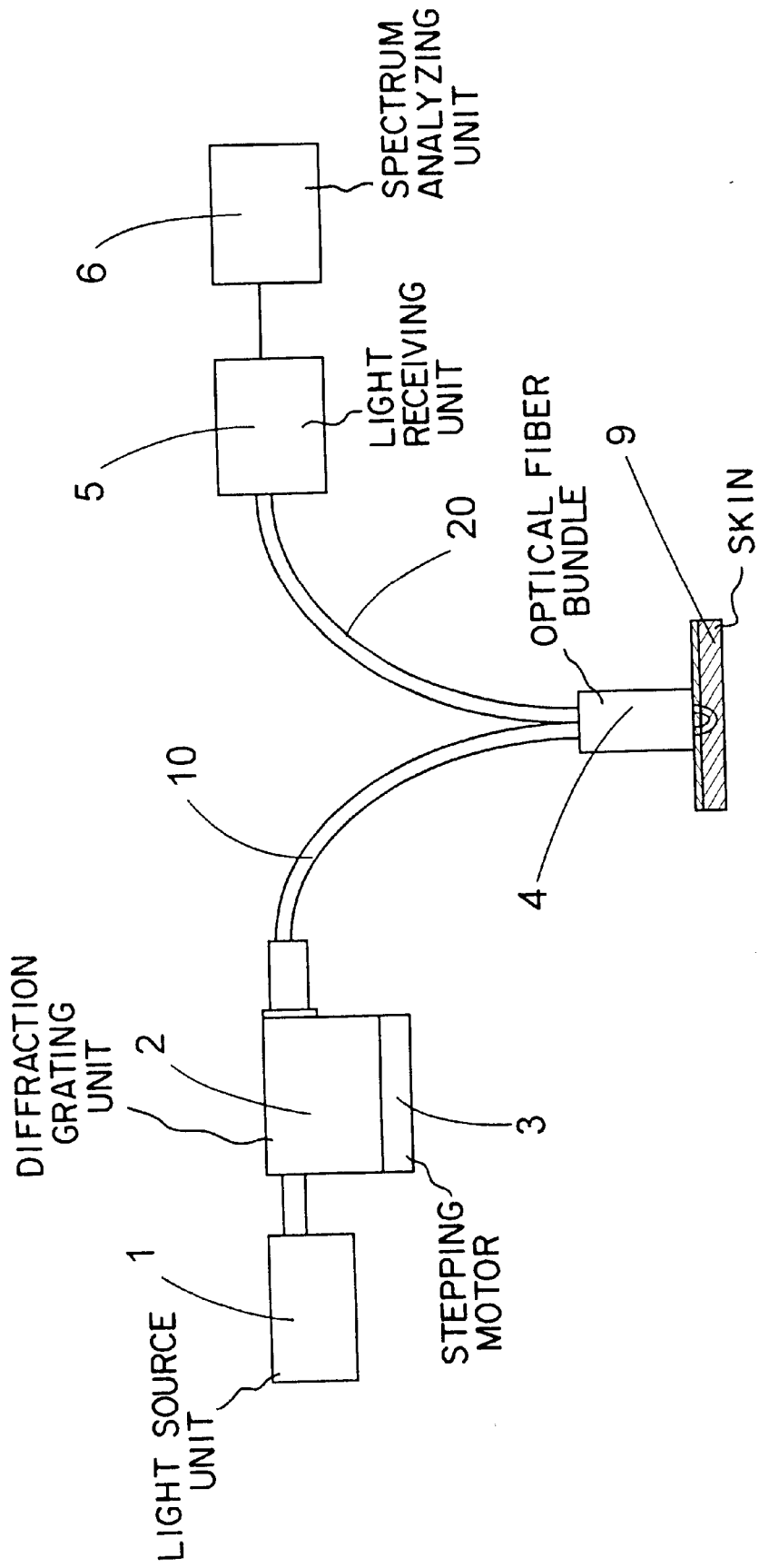
FIG. 1 is a schematic diagram of a device for non-invasive determination of a glucose concentration in the blood of a subject of a first embodiment of the present invention.

A device for non-invasive determination of a glucose concentration in the blood of a subject of the present invention is shown in FIG. 1. The device is formed with a light source unit comprising a halogen lamp 1 of about 150 W, a diffraction grating unit 2 as a spectroscope of a light provided from the halogen lamp, and a stepping motor unit 3 for controlling a rotation angle of the diffraction grating to provide near-infrared radiation, an optical fiber bundle 4 having a plurality of first optical fibers 10 for projecting the near-infrared radiation on a skin 9 of the subject and a plurality of second optical fibers 20 for receiving the resulting radiation emitted from the skin, a light receiving unit 5 connected to the second optical fibers, and a spectrum analyzing unit 6 for making a spectrum analysis of the resulting radiation and determining the glucose concentration in the blood of the subject according to the spectrum analysis.

Figure 2:
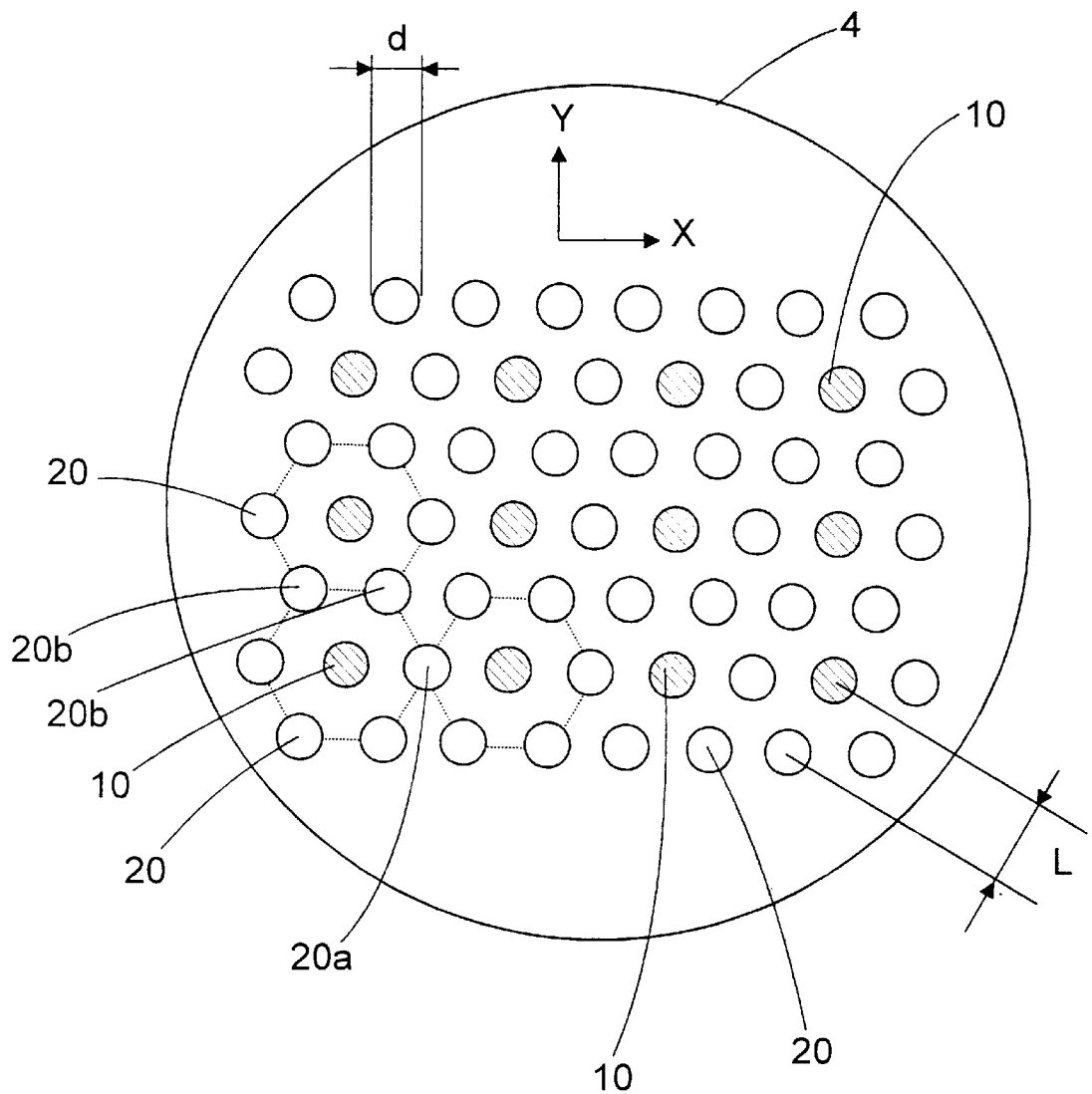
FIG. 2 is an end view of an optical fiber bundle of the first embodiment.

Each of the first optical fibers 10 is connected at its one end to the light source unit, and provides the near-infrared radiation from its opposite projection end. Each of the second optical fibers 20 is connected at its one end to the light receiving unit 5, and receives the resulting radiation at its opposite receiving end. The optical fiber bundle 4 has an end surface at which the bundle is pressed against the skin. It is preferred to use a pressure gauge and a fixture for pressing the optical fiber bundle 4 against the skin by a required pressure. The projection ends of the first optical fibers 10 and the receiving ends of the second optical fibers 20 are exposed on the end surface of the optical fiber bundle 4. As shown in FIG. 2, the optical fiber bundle 4 is formed with a plurality of sub-bundles, in each of which a projection end of the first optical fiber 10 is disposed on the end surface of the bundle at a center of a hexagonal pattern, as shown by a dotted line in FIG. 2, and six receiving ends of the second optical fibers 20 are disposed at corners of the hexagonal pattern. A receiving end 20a of each of the sub-bundles is common with an adjacent sub-bundle in an X-axis direction. Two receiving ends 20b of each of the sub-bundles are common with an adjacent sub-bundle in a Y-axis direction.

In each of the sub-bundles, a distance L between a center of the projection end of the first optical fiber 10 and a center of an adjacent receiving end of the second optical fiber 20 is determined within a range of 0.1 mm to 2 mm, and more preferably a range of 0.2 mm to 1 mm, to selectively receive the resulting radiation emitted from a dermis layer of the skin 9. When the distance L is less than 0.1 mm, the resulting radiation contains a large amount of spectrum information of an epidermis layer of the skin 9. On the other hand, as the distance L is more than 2 mm, spectrum information of a subcutaneous tissue layer positioned under the dermis layer increases. Variations in glucose concentration of the dermis layer is smaller than those of the epidermis layer and the subcutaneous tissue layer. The present device is directed to selectively extract spectrum information of the dermis layer and determine the glucose concentration in the blood of the subject according to the spectrum information. In this embodiment, the first and second optical fibers (10, 20) have a same diameter d of 200 $\mu$m, and the distance L is 500 $\mu$m. In the present invention, it is preferred to use first and second optical fibers each having a diameter within a range of 70 $\mu$m and 1000 $\mu$m.

Figure 3:
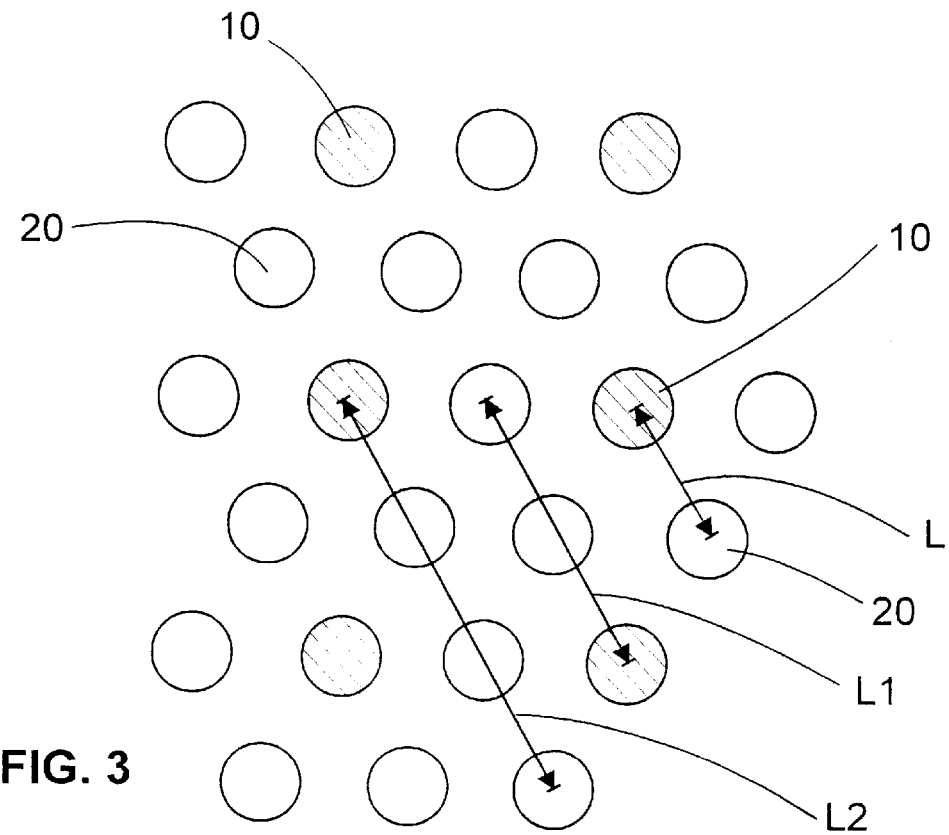
FIG. 3 is a partially enlarged view of FIG. 2.
Figure 4:
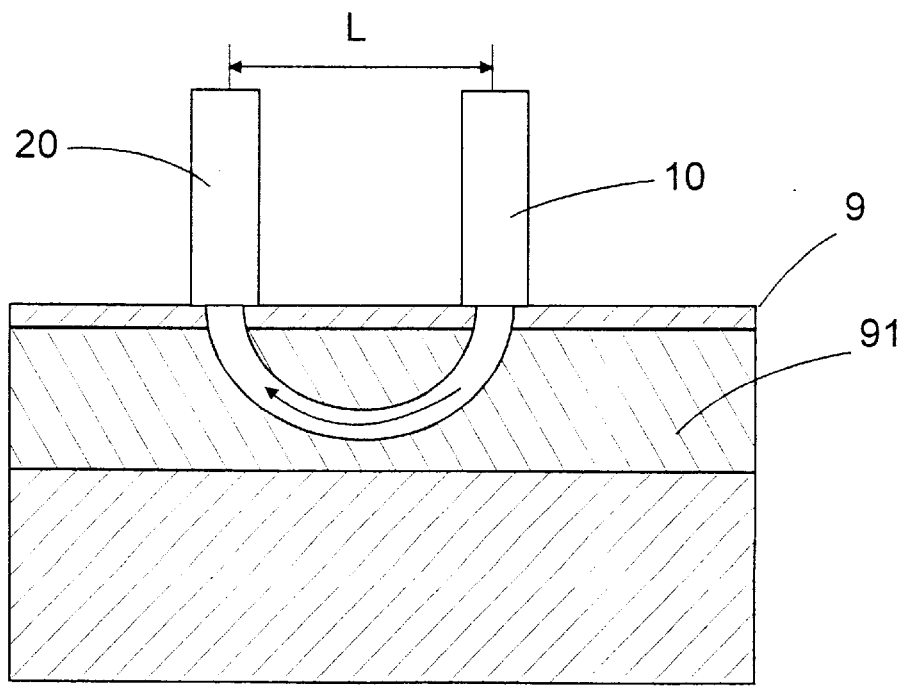
FIG. 4 is a schematically cross-sectional view of a light path passing through a skin between a projection end and an adjacent receiving end.

By the way, when the receiving ends of the second optical fibers 20 are disposed, as shown in FIG. 2, there are a lot of combinations as to the distance between the projection end and the receiving end. For example, as shown in FIG. 3, a distance L1 between a projection end of a hexagonal pattern and a receiving end of an adjacent hexagonal pattern is about two times of the distance L. In addition, a distance L2 between a projection end of a hexagonal pattern and a receiving end of a further-spaced hexagonal pattern is about three times of the distance L. A light path formed through the skin 9 between a projection end and a receiving end separated therefrom by the distance L is schematically shown in FIG. 4. In an optically-opaque, complex skin structure, it would be difficult to precisely discuss about light-transmission and light-scattering phenomena according to Lambert-Beer's law. However, as a total length of the light path increases, a light amount to be received is rapidly decreased. For example, when a light path is twice as long as the light path formed between the distance L, the light amount would be decreased to $\frac{1}{10}$ or less. When a light path is three times as long as the light path formed between the distance L, the light amount would be decreased to $\frac{1}{100}$ or less. Therefore, the light amount received by each of the receiving ends would be substantially equal to a total of light amount provided by light paths formed between the receiving end and adjacent projection ends separated therefrom by the distance L. In the present invention, since the distance L is determined such that each of the light paths is mostly formed in the dermis layer 91, as shown in FIG. 4, it is possible to selectively detect the spectrum information of the dermis layer.

The light receiving unit 5 comprises a photo-diode made of In-Ga-As and having a wavelength-sensitivity of 0.9 $\mu$m to 1.7 $\mu$m, amplifier and an A/D converter. Alternatively, a conventional light receiving unit can be used. The spectrum analyzing unit 6 comprises a microcomputer, in which a multivariate analysis is performed by the use of adsorption spectrum of near-infrared radiation of 1.25 $\mu$m to 1.7 $\mu$m. A calibration line (or calibration equation) obtained by a PLS (Partial Least Square) regression analysis is used to the multivariate analysis. For example, the calibration line can be obtained by the PLS regression analysis using two variables. One of the variables is data of the adsorption spectrum which are obtained from test subjects, and the other one is data of the glucose concentration in dermis layer which are measured from the test subjects by an invasive method. Thus, a first statistically-obtained correlation between the adsorption spectrum and the glucose concentration in dermis layer and a second statistically-obtained correlation between the glucose concentration in dermis layer and the glucose concentration in blood are used in the spectrum analyzing unit 6.

The light source unit provides near-infrared radiation having successive wavelengths within a range of 1300 nm to 2500 nm. When the wavelength is less than 1300 nm, it is difficult to obtain the resulting radiation having a good S/N ratio. Near-infrared radiation having wavelengths less than 1300 nm shows excellent transmittance in a living body. In other words, an absorption of the near-infrared radiation in the living body is very small. Therefore, when a projection end of the first optical fiber 10 is spaced from an adjacent receiving end of the second optical fiber 20 by the distance L within the range of 0.1 mm to 2 mm, it would be difficult to obtain the resulting radiation including a sufficient amount of spectrum information of the dermis layer by the use of near-infrared radiation having wavelengths less than 1300 nm. In particular, it is preferred to use the near-infrared radiation having at least one of successive wavelengths from 1400 nm to 1800 nm, and successive wavelengths from 2000 nm to 2500 nm.

Figure 5:
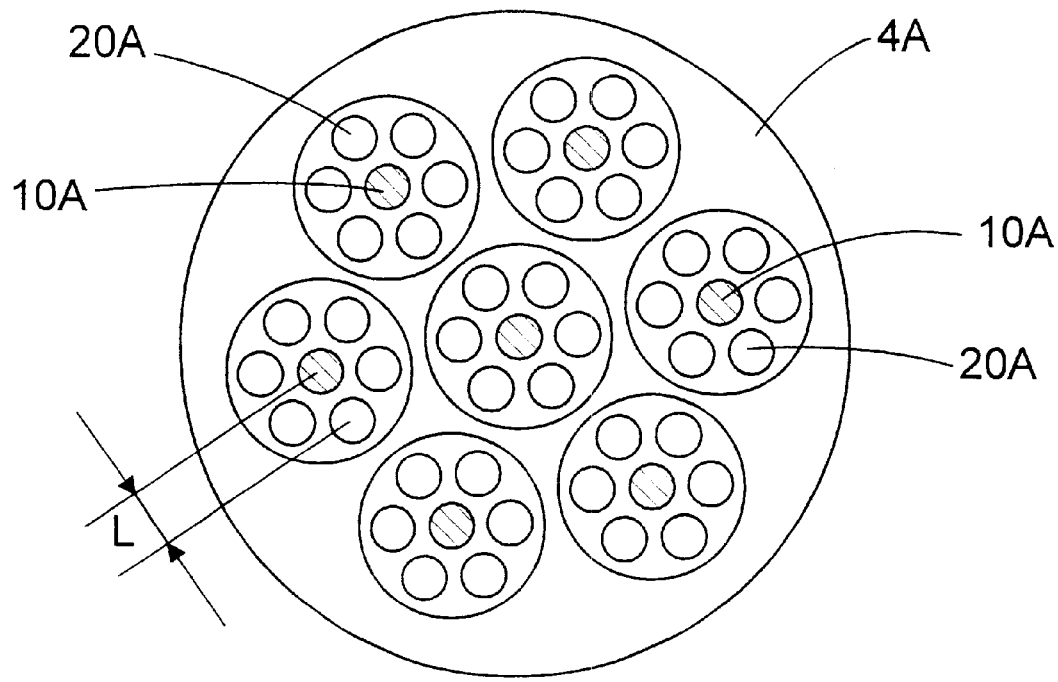
FIG. 5 is an end view of an optical fiber bundle of a first modification of the first embodiment.

As a first modification of the first embodiment, it is possible to use an optical fiber bundle 4A having a plurality of sub-bundles, as shown in FIG. 5. In each of the sub-bundles, a projection end of a first optical fiber 10A is disposed at a center of a hexagonal pattern, and six receiving ends of second optical fibers 20A are disposed at corners of the hexagonal pattern. This modification differs from the first embodiment in that each of the sub-bundles is independent from an adjacent sub-bundle without having a common receiving end. A distance L between the projection end and an adjacent receiving end is adequately determined to fall within the range of 0.1 mm to 2 mm.

Figure 6A:
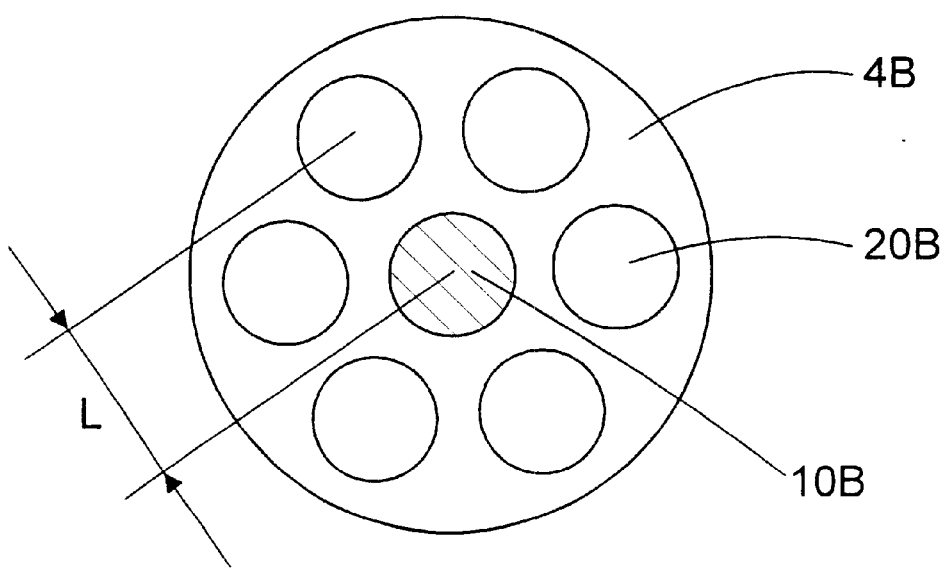
FIG. 6A is an end view of an optical fiber bundle of a second modification of the first embodiment.
Figure 6B:
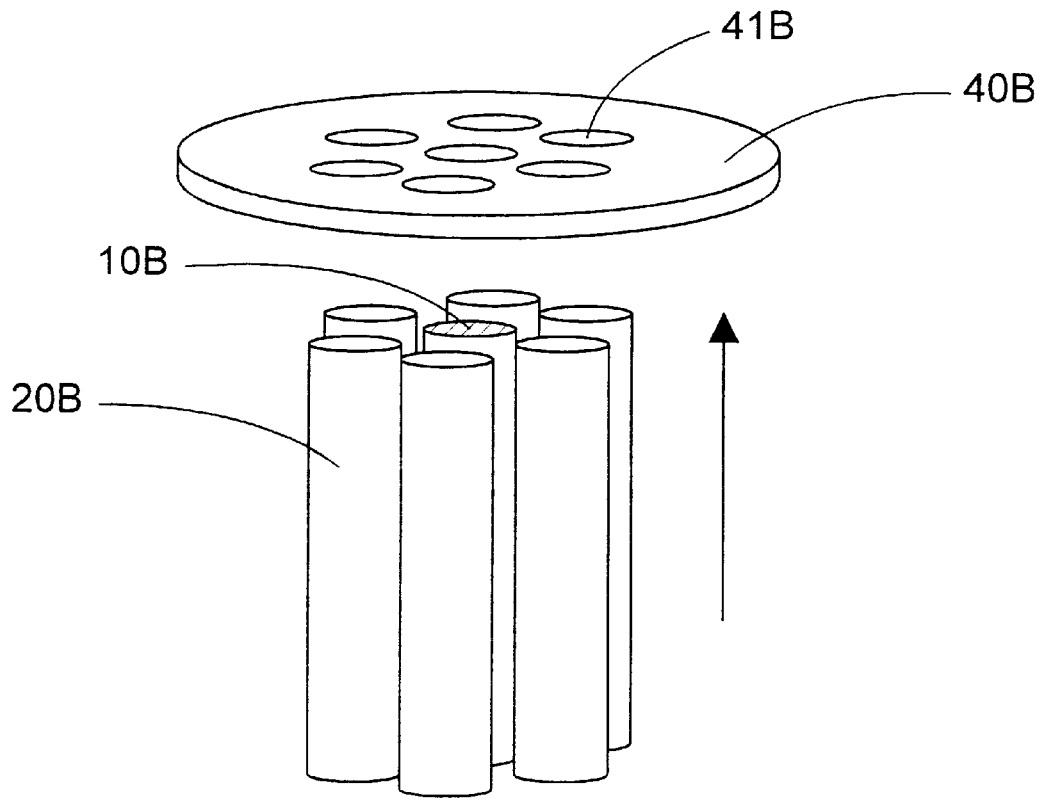
Figure 6C:
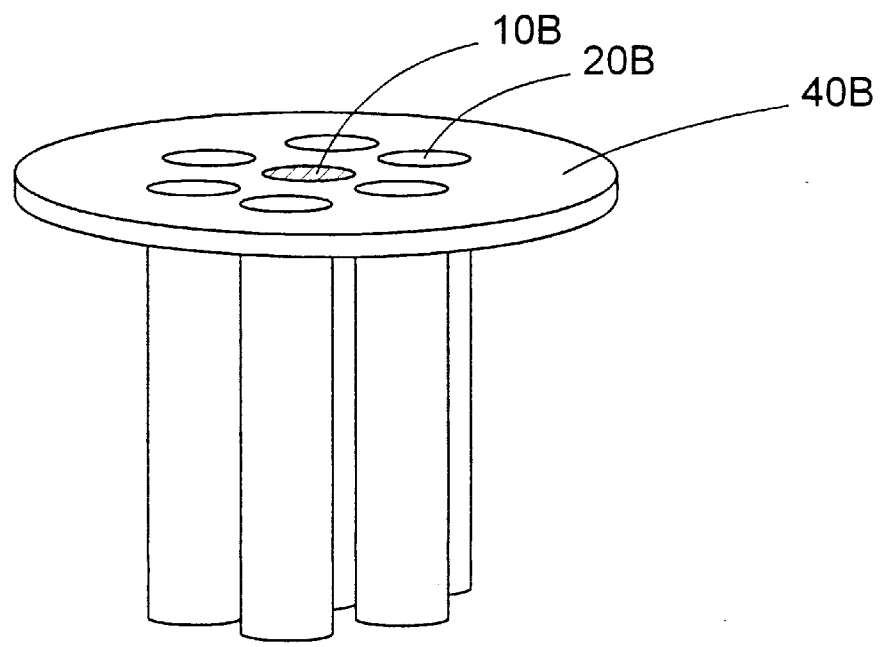
Figure 7:
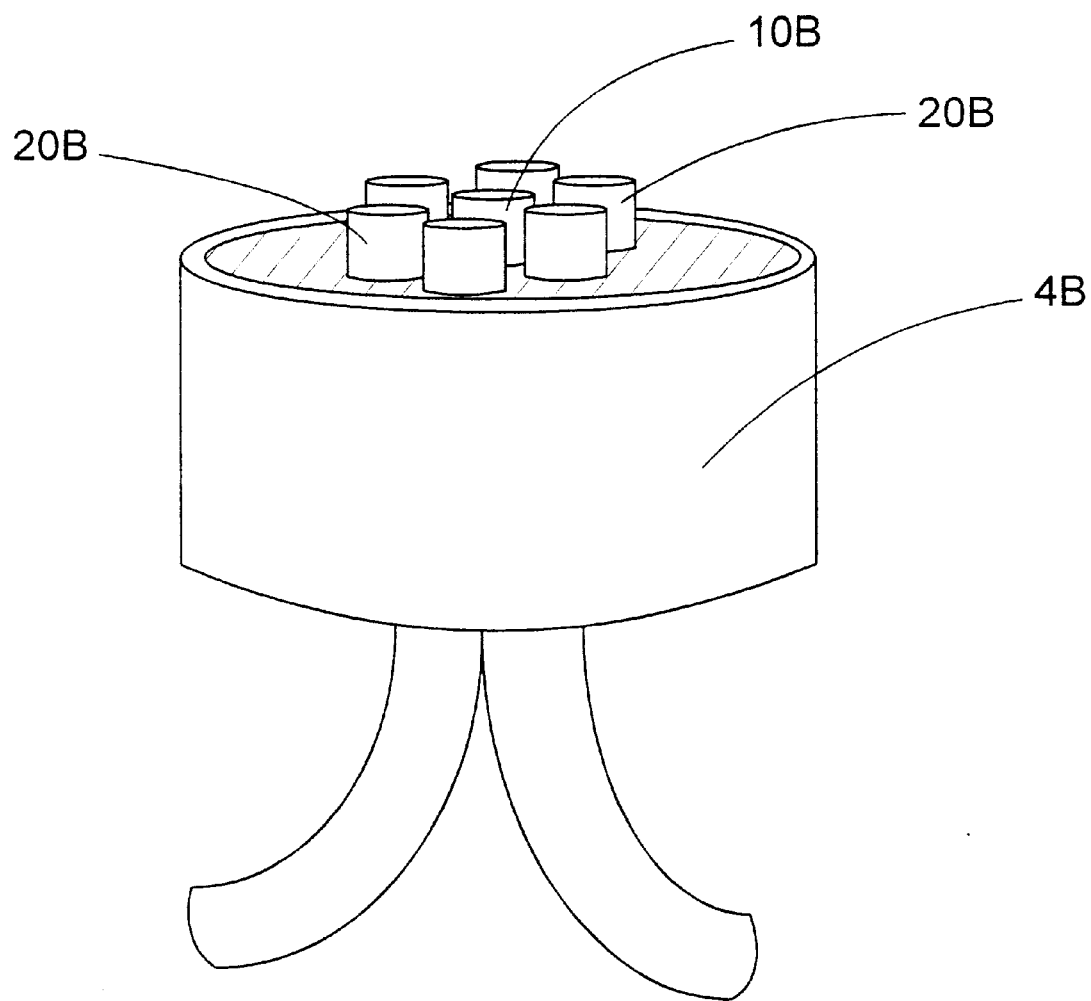
FIG. 7 is a perspective view of an optical fiber bundle of the second modification.

As a second modification of the first embodiment, it is possible to use an optical fiber bundle 4B, as shown in FIG. 6A. That is, the optical fiber bundle 4B is formed with a single projection end of a first optical fiber 10B disposed at a center of a hexagonal pattern and six receiving ends of second optical fibers 20B disposed at corners of the hexagonal pattern. For example, the optical fiber bundle 4B can be formed by preparing a circular plate 40B having a plurality of through holes 41B arranged in the hexagonal pattern, as shown in FIG. 6B, and inserting the first ad second optical fibers (10B, 20B) into the through holes, as shown in FIG. 6C. It is preferred that the projection and receiving ends of the first and second optical fibers (10B, 20B) are slightly projected from an end surface of the optical fiber bundle 4B, as shown in FIG. 7, to achieve a complete contact between the skin and the projection and receiving ends. In this modification, each of the first and second optical fibers (10B, 20B) has a diameter of 200 $\mu$m. A distance L between the projection end and the adjacent receiving end is adequately determined to fall within the range of 0.1 mm to 2 mm.

Second Embodiment

Figure 8:
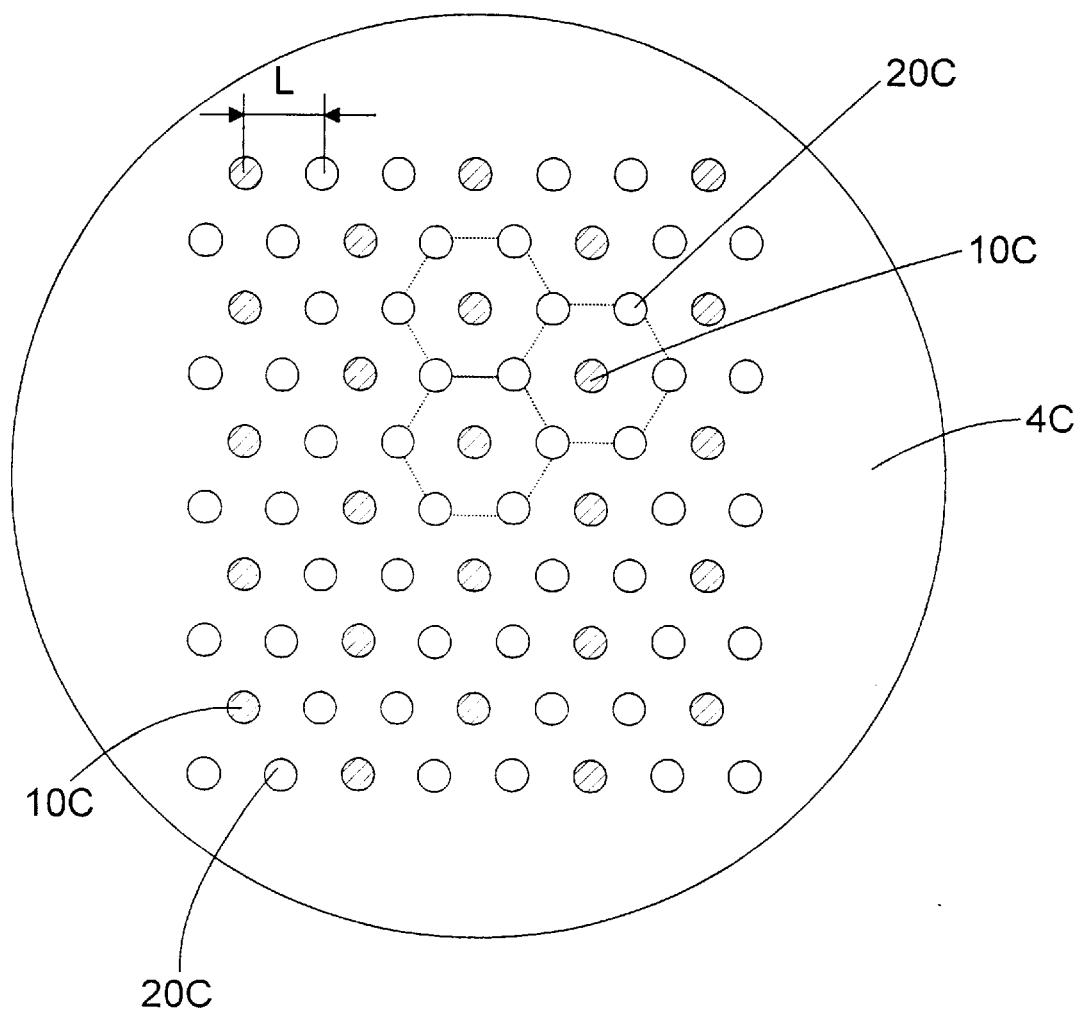
FIG. 8 is an end view of an optical fiber bundle of a second embodiment.

A device for non-invasive determination of a glucose concentration in the blood of a subject of a second embodiment of the present invention is identical to that of the first embodiment except for a different pattern of sub-bundles of an optical fiber bundle 4C. That is, as shown in FIG. 8, two receiving ends of second optical fibers 20C of each of the sub-bundles are common with an adjacent sub-bundle. In this embodiment, each of first and second optical fibers (10C, 20C) has a diameter of 200 $\mu$m. In each of the sub-bundles, a distance L between a center of a projection end of the first optical fiber 10C and a center of an adjacent receiving end of the second optical fiber 20C is 650 $\mu$m.

Figure 9:
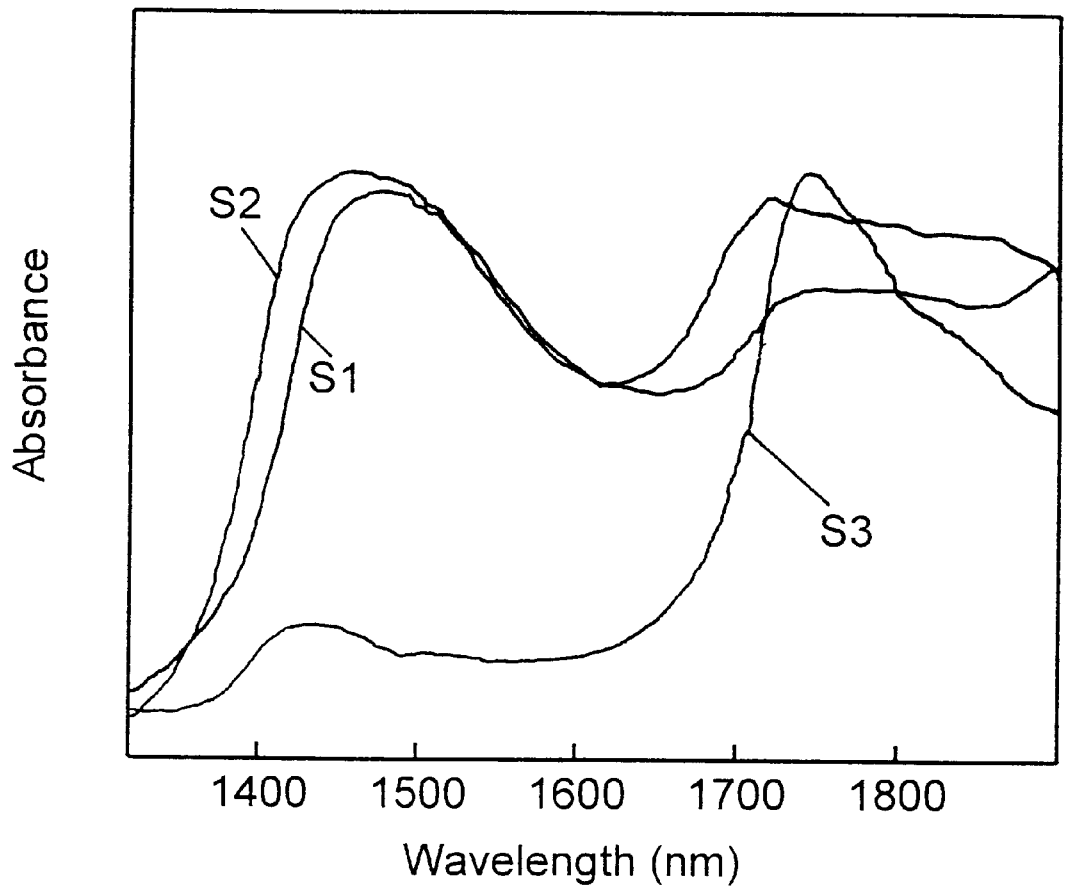
FIG. 9 is a spectrum diagram showing results of an experiment explained in the second embodiment.

To show an advantage of the optical fiber bundle 4C, an experiment was performed by the use of a phantom which is composed of an imitational epidermis layer having a thickness of about 50 $\mu$m as a top layer, an imitational dermis layer having a thickness of about 1 mm as an intermediate layer, and a lard layer having a thickness of about 1 cm as a bottom layer. The imitational epidermis and dermis layers are formed to have substantially same optical properties as the epidermis and dermis layers of the human skin. The lard layer is used as an imitational subcutaneous-tissue layer. In FIG. 9, an adsorption spectrum S1 was measured by vertically pressing the optical fiber bundle 4C against the top surface of the phantom. A comparative experiment was performed by the use of an optical fiber bundle which is substantially a same as the optical fiber bundle of FIG. 8 except that a distance between centers of a projection end and an adjacent receiving end is 6000 $\mu$m. In FIG. 9, an adsorption spectrum S2 was measured by vertically pressing the comparative bundle against the top surface of the phantom. FIG. 9 also shows an adsorption spectrum S3 of the lard layer. The spectrum S3 of the lard layer has a large, relatively-sharp peak at the vicinity of 1730 nm, and a small, relatively-broad peak at the vicinity of 1420 nm. The spectrum S2 is influence by these two peaks of the lard layer. On the other hand, the influence of the two peaks to the spectrum S1 is much smaller than the former case. From these considerations, it is suggested that the optical fiber bundle 4C of the present invention can selectively provide an absorption spectrum of the dermis layer, while minimizing the influence of undesirable spectrum information from the subcutaneous tissue layer.

Figure 10:
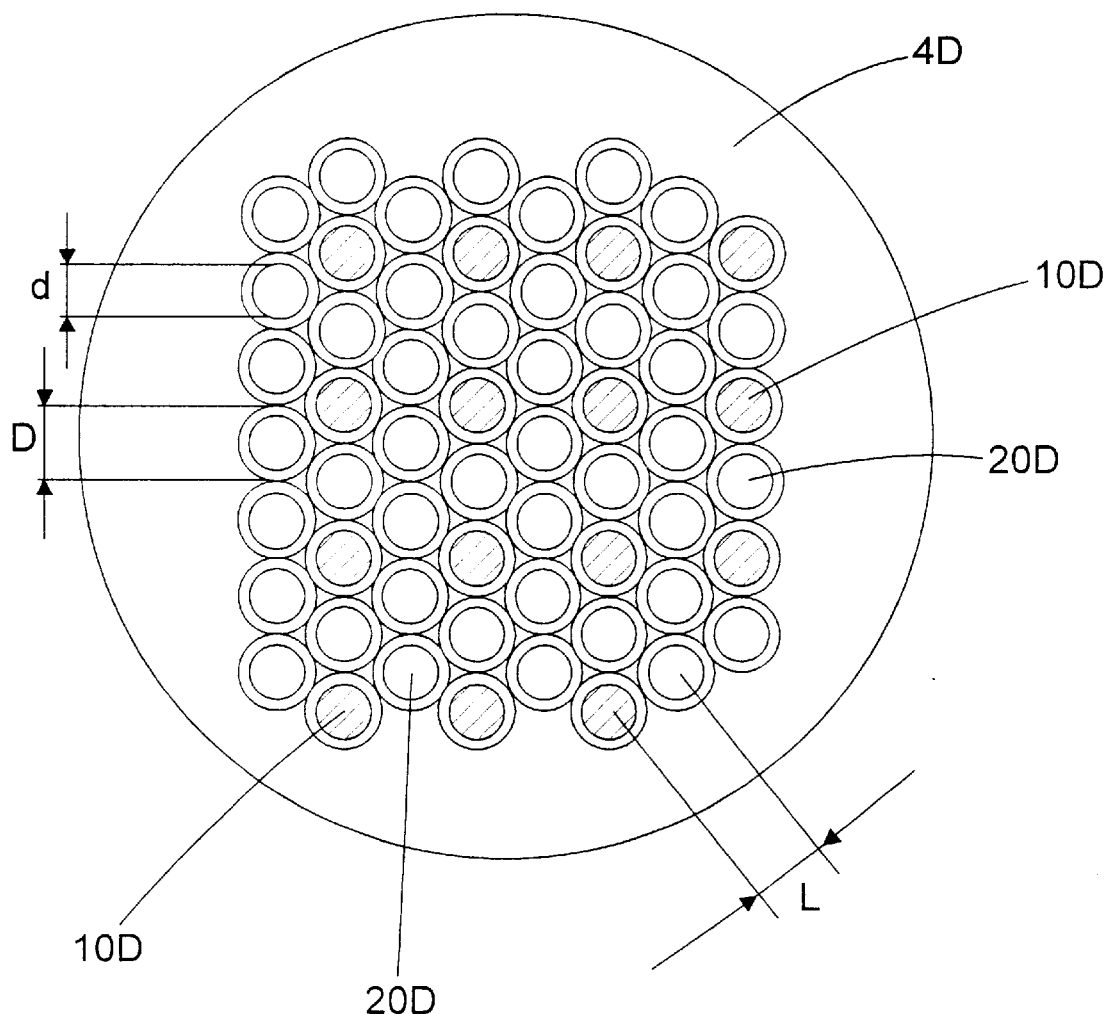
FIG. 10 is an end view of an optical fiber bundle of a first modification of the second embodiment.

As a first modification of the second embodiment, it is possible to use an optical fiber bundle 4D, as shown in FIG. 10. The optical fiber bundle 4D is formed with a plurality of sub-bundles, in each of which a projection end of a first optical fiber 10D is disposed at a center of a hexagonal pattern and six receiving ends of second optical fibers 20D are disposed at corners of the hexagonal pattern. Two receiving ends of each of the sub-bundles is common with an adjacent sub-bundle. Each of the first and second optical fibers (10D, 20D) has a diameter d of 250 $\mu$m, and is covered by a nylon tube having an outer diameter D of 500 $\mu$m. Therefore, a distance L between centers of a projection end and an adjacent receiving end is 500 $\mu$m. A ratio of the number of the first optical fibers 10D to the number of the second optical fibers 20D is about 1:2.

Third Embodiment

Figure 11:
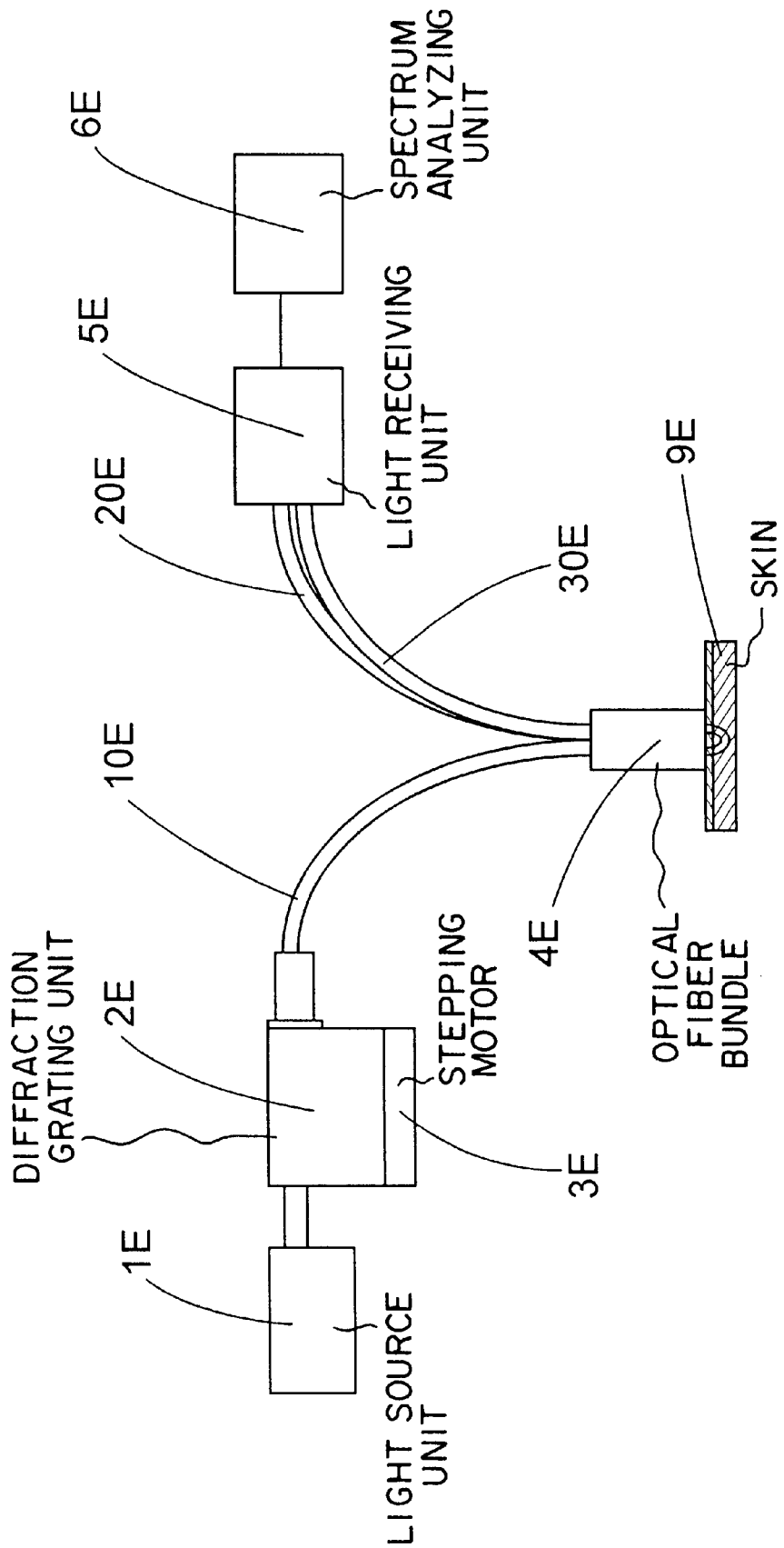
FIG. 11 is a schematic diagram of a device for non-invasive determination of a glucose concentration in the blood of a subject of a third embodiment of the present invention.
Figure 12:
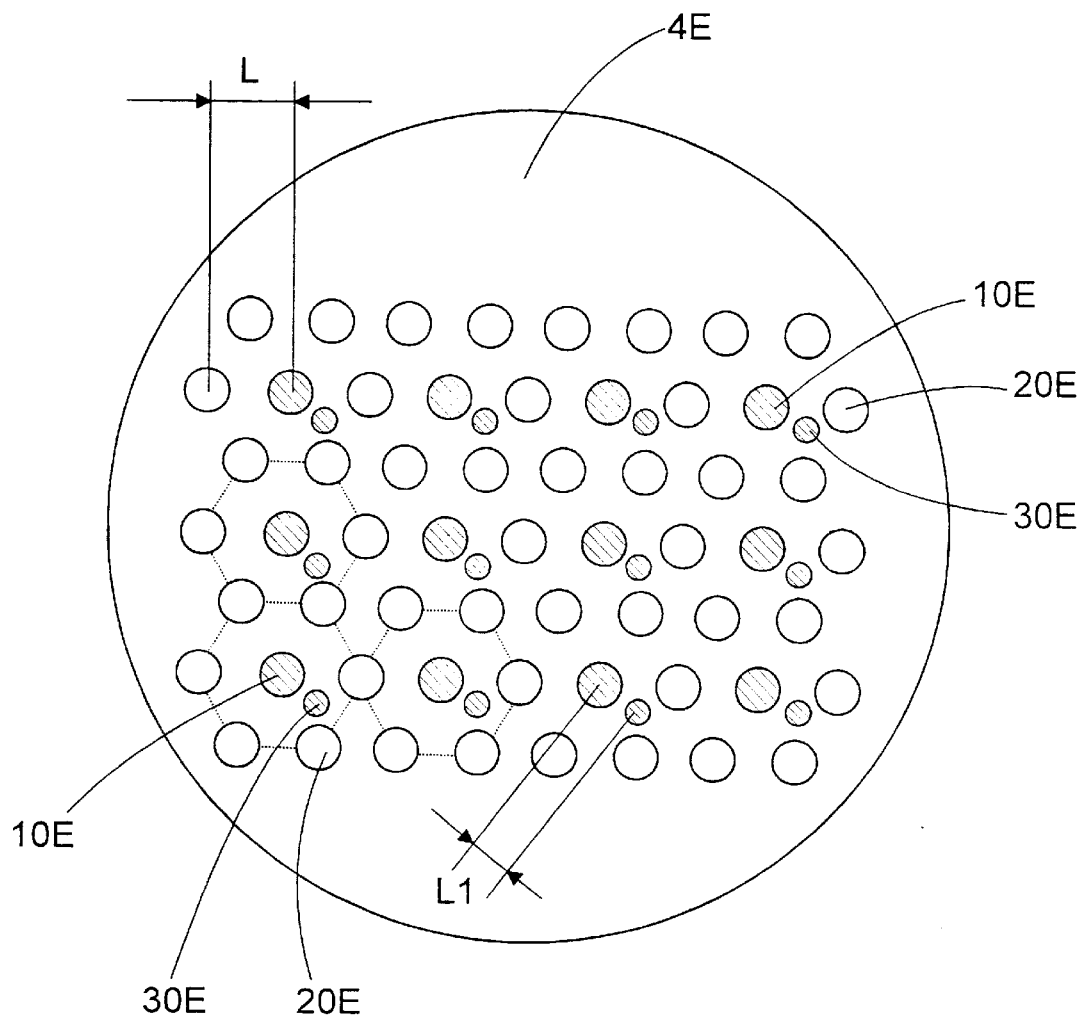
FIG. 12 is an end view of an optical fiber bundle of the third embodiment.

A device for non-invasive determination of a glucose concentration in the blood of a subject of a third embodiment of the present invention is identical to that of the first embodiment except for the following features. Therefore, no duplicate explanation to common parts and operation is deemed necessary. As shown in FIG. 11, an optical fiber bundle 4E comprises a plurality of third optical fibers 30E for selectively receiving a resulting radiation emitted from an epidermis layer of a skin of the subject. A diameter of the third optical fibers is 100 $\mu$m. Each of the third optical fibers 30E is connected at its one end to a light receiving unit 5E. In each of hexagonal pattern; of sub-bundles of the optical fiber bundle 4E, as shown in FIG. 12, a receiving end of the third optical fiber 30E is disposed between a projection end of a first optical fiber 10E and one of receiving ends of second optical fibers 20E. A distance L between the projection end and the receiving end of the second optical fiber 20E is adequately determined to fall within the range of 0.1 mm to 2 mm. A distance L1 between the projection end and an adjacent receiving end of the third optical fiber 30E is determined to be lower than the distance L. In the present invention, the resulting radiation received by the second optical fibers 20E selectively contains the spectrum information of a dermis layer of the skin, however, a small amount of spectrum information of the epidermis layer is inevitably included in the resulting radiation. The third optical fibers 30E are preferably used to subtract the spectrum information of the epidermis layer from the resulting radiation received by the second optical fibers 20E. As a result, it is possible to achieve an accurate spectrum analysis of the resulting radiation, while minimizing the influence of the spectrum information of the epidermis layer.

Fourth Embodiment

Figure 13:
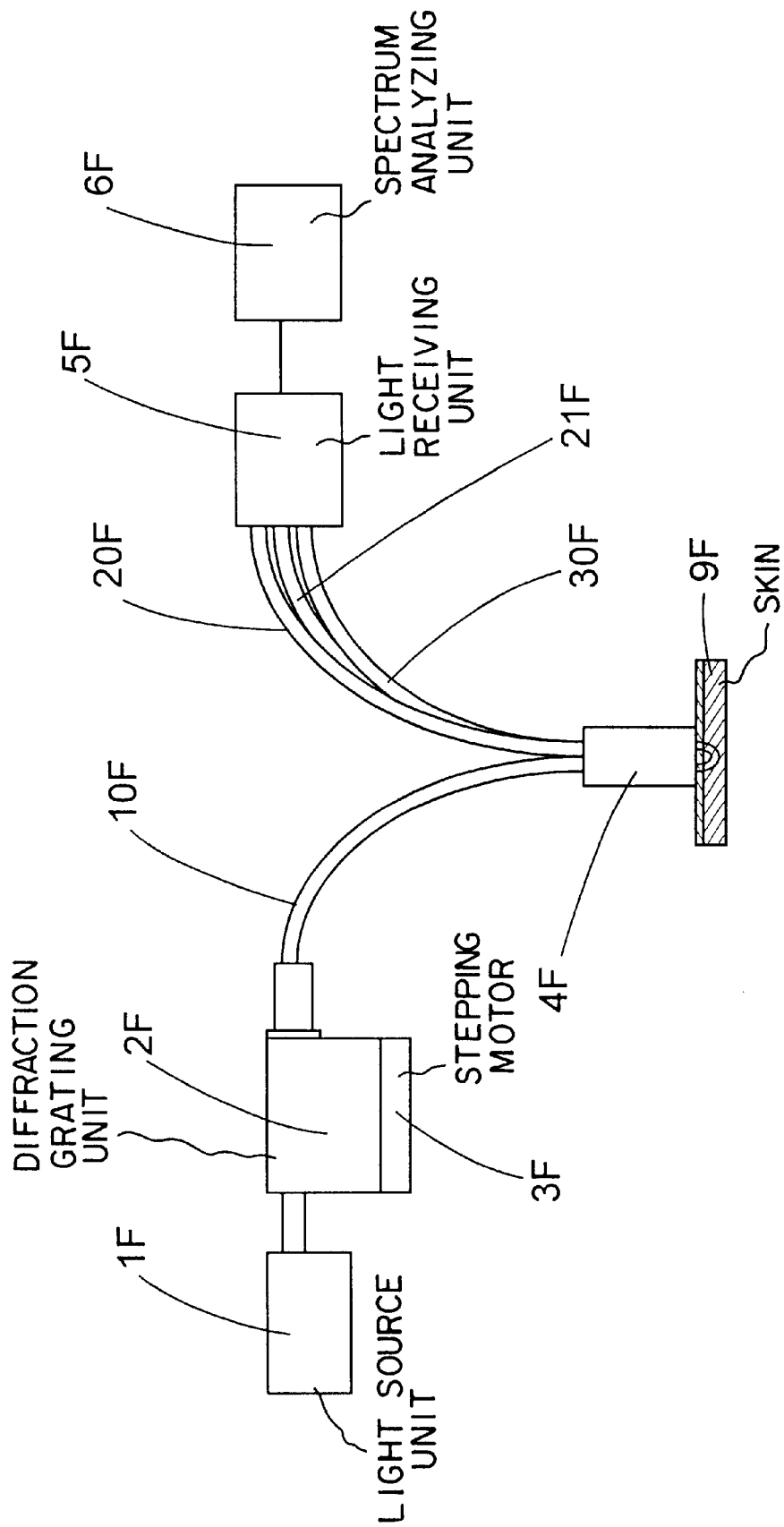
FIG. 13 is a schematic diagram of a device for non-invasive determination of a glucose concentration in the blood of a subject of a fourth embodiment of the present invention.
Figure 14:
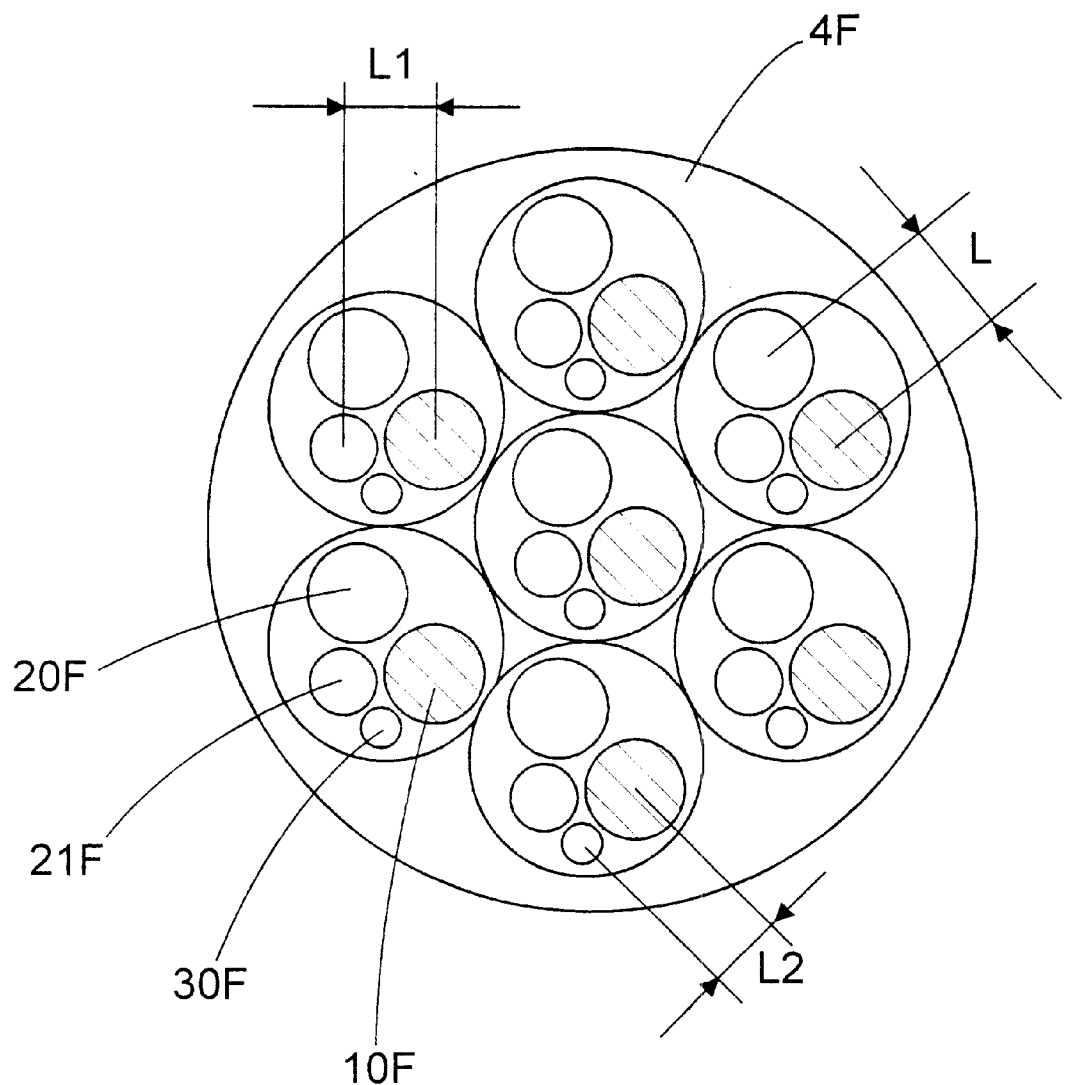
FIG. 14 is an end view of an optical fiber bundle of the fourth embodiment.

A device for non-invasive determination of a glucose concentration in the blood of a subject of a fourth embodiment of the present invention is identical to that of the first embodiment except for the following features. Therefore, no duplicate explanation to common parts and operation is deemed necessary. As shown in FIGS. 13 and 14, an optical fiber bundle 4F is formed with a plurality of sub-bundles, each of which is composed of a first optical fiber 10F having a diameter of 500 μm, two second optical fibers (20F, 21F) having diameters of 500 μm and 250 μm, and a third optical fiber 30F having a diameter of 100 μm. In each of the sub-bundles, a projection end of the first optical fiber 10F is disposed on an end surface of the optical fiber bundle 4F at an eccentric point of a circular pattern, and two receiving ends of the second optical fibers (20F, 21F) are disposed adjacent to the projection end in the circular pattern. The third optical fibers 30F are connected to a light receiving unit 5F. A receiving end of each of the third optical fibers 30F is disposed on the end surface of the optical fiber bundle 4F in the circular pattern so as to be closer to the projection end than the receiving ends of the second optical fibers (20F, 21F).

Figure 15:
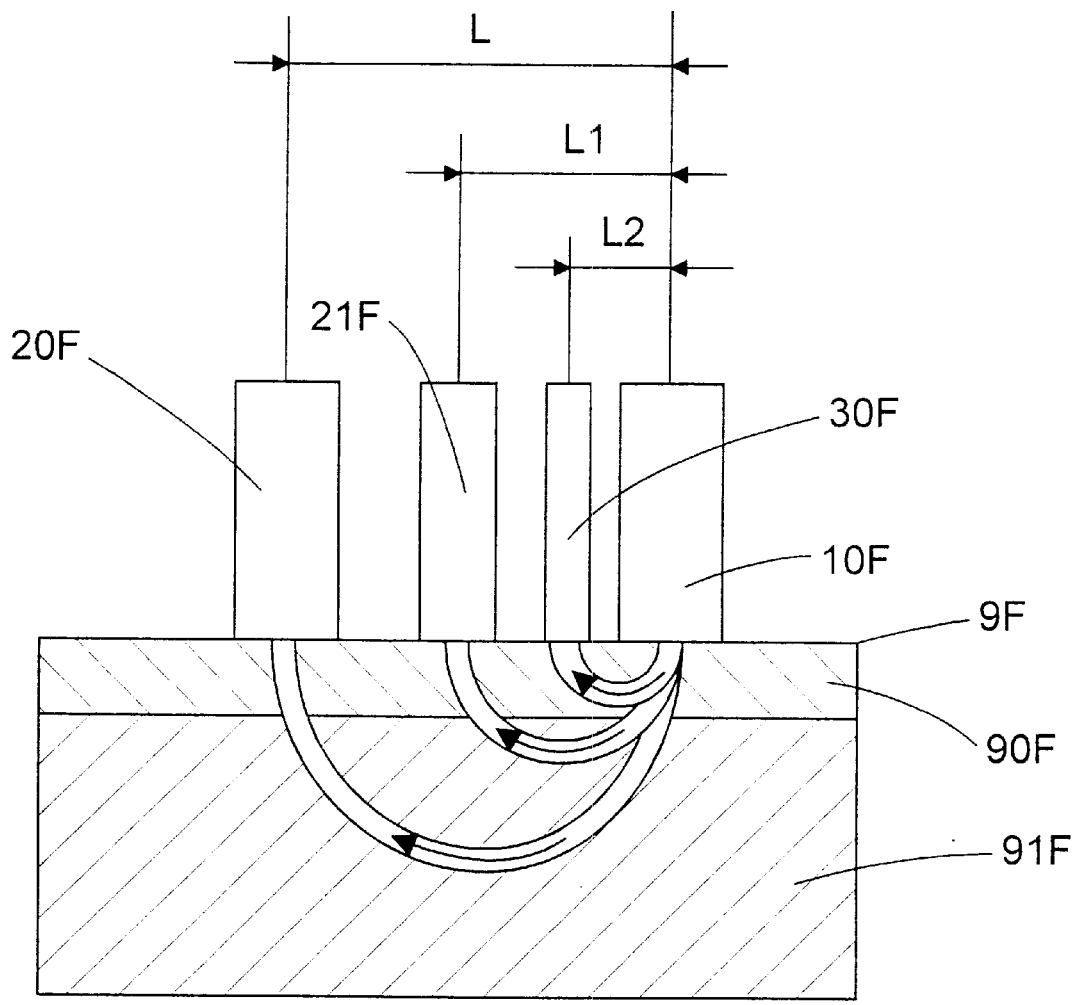
FIG. 15 is a schematically cross-sectional view showing three different light paths directing from a projection end to receiving ends through a skin.

As shown in FIG. 15A, a distance L between a projection end and a receiving end of the second optical fiber 20F of 500 μm is determined to fall within the range of 0.1 mm to 2 mm such that the receiving end can selectively sense the resulting radiation emitted from a center portion of a dermis layer 91F of a skin 9F. A distance L1 between the projection end and a receiving end of the second optical fiber 21F of 250 μm is determined such that the receiving end can selectively sense the resulting radiation emitted from an upper portion of the dermis layer 91F adjacent to an interface between the dermis layer and an epidermis layer 90F of the skin 9F. The distance L1 is determined to fall within the range of 0.1 mm to 2 mm and be smaller than the distance L. A distance L2 between the projection end and a receiving end of the third optical fiber 30F is determined such that the receiving end can selectively sense the resulting radiation emitted from the epidermis layer 90F. The distance L2 is smaller than the distance L1. As a result, it is possible to perform the spectrum analysis according to an adsorption spectrum of only the dermis layer 91E by the use of subtractions of adsorption spectra obtained through the second and third optical fibers (20F, 21F, 30F). If necessary, the diameters of the first to third optical fibers (10F, 20F, 21F, 30F) will be adequately changed.

Figure 16:
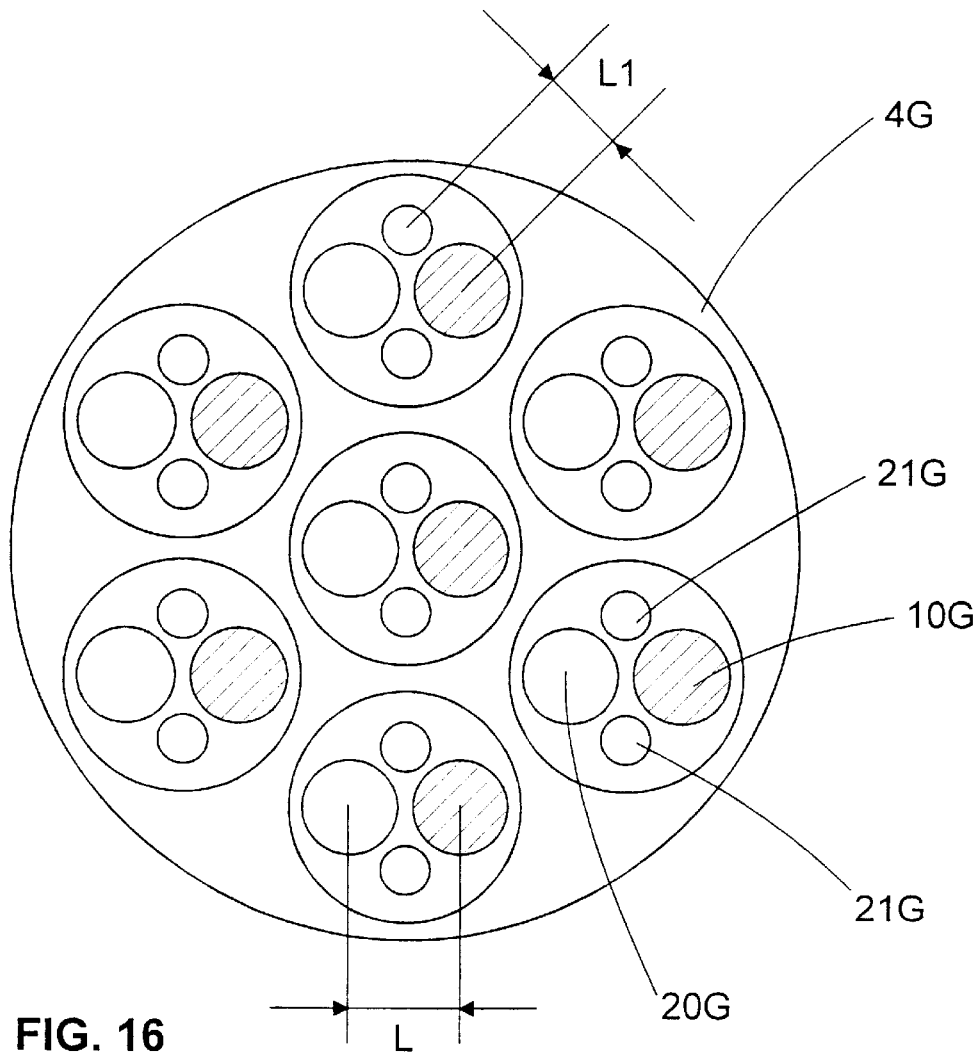
FIG. 16 is an end view of an optical fiber bundle of a first modification of the fourth embodiment.

As a first modification of the fourth embodiment, it is possible to use an optical fiber bundle 4G having a plurality of sub-bundles, as shown in FIG. 16. In this modification, the number of the sub-bundles is seven. Each of the sub-bundles is composed of a first optical fiber 10G having a diameter of 500 μm, and three of second optical fibers (20G, 21G). One of the second optical fibers 20G is of a diameter of 500 μm, and the rest of the second optical fibers 21G are of a diameter of 250 μm. A distance L between a projection end and a receiving end of the second optical fiber 20G of 500 μm, and a distance L1 between the projection end and a receiving end of the second optical fibers 21G of 250 μm, are adequately determined to fall within the range of 0.1 mm to 2 mm such that the distance L is larger than the distance Li.

Figure 17:
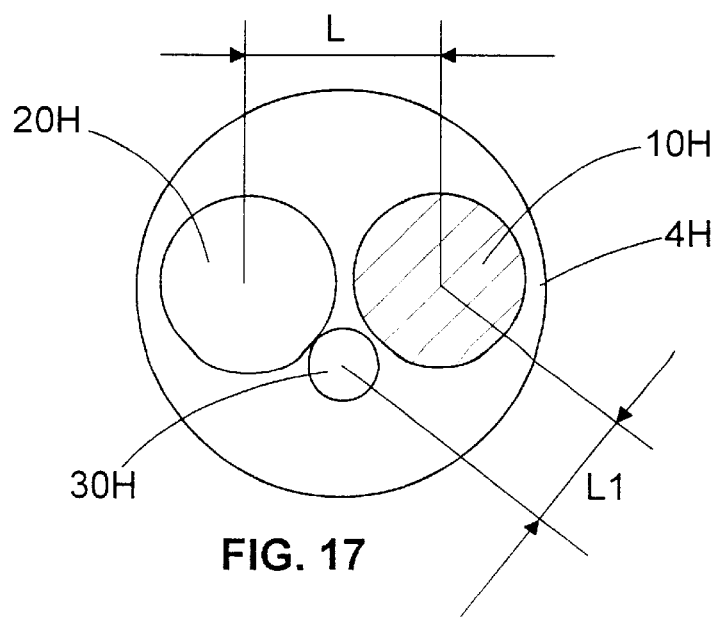
FIG. 17 is an end view of an optical fiber bundle of a second modification of the fourth embodiment.

As a second modification of the fourth embodiment, it is possible to use an optical fiber bundle 4H, as shown in FIG. 17. The optical fiber bundle 4H is composed of a first optical fiber 10H, a second optical fiber 20H having a same diameter as the first optical fiber, and a third optical fiber 30H having a smaller diameter than the first optical fiber. In FIG. 17, a distance L between a projection end of the first optical fiber 10H and a receiving end of the second optical fiber 20H is determined to fall within the range of 0.1 mm to 2 mm such that the receiving end can selectively sense the resulting radiation emitted from the dermis layer. On the other hand, a distance L1 between the projection end and a receiving end of the third optical fiber 30H is determined to be smaller than the distance L such that the receiving end can selectively sense the resulting radiation emitted from the epidermis layer.

Fifth Embodiment

Figure 18:
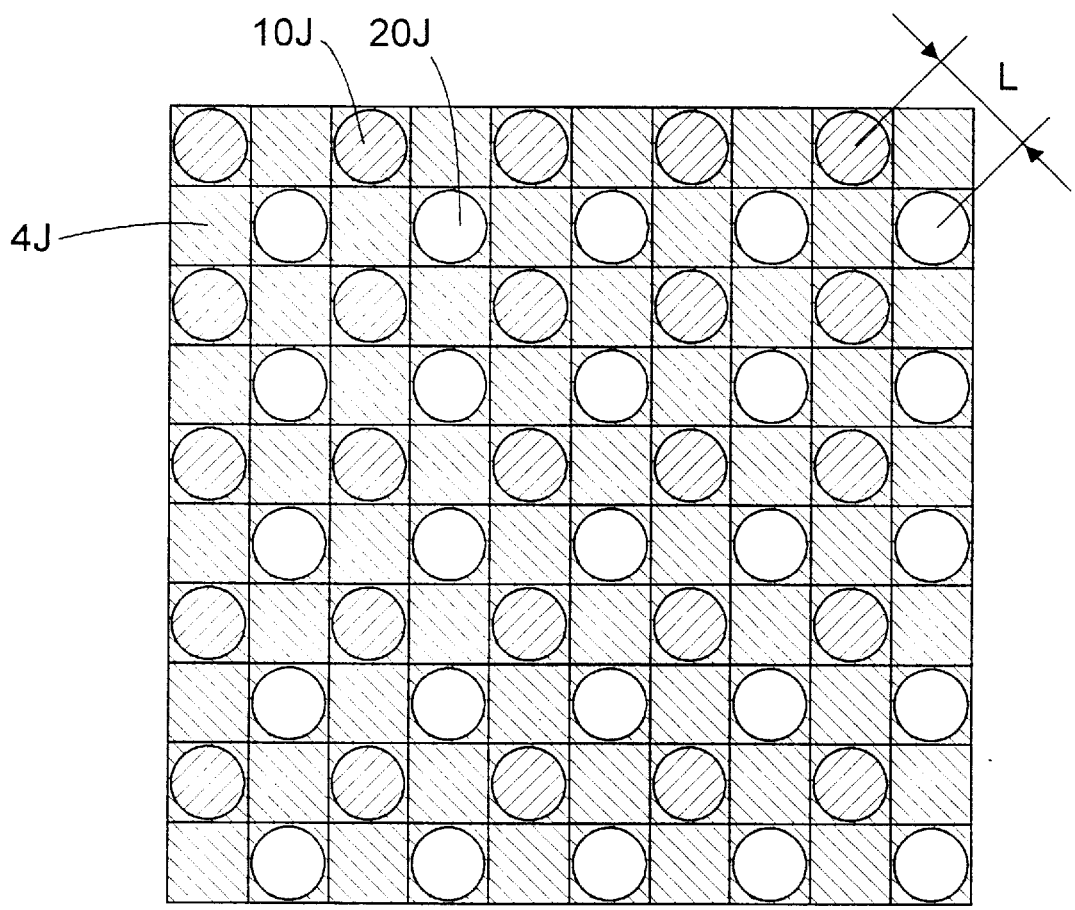
FIG. 18 is an end view of an optical fiber bundle of a fifth embodiment.

A device for non-invasive determination of a glucose concentration in the blood of a subject of a fifth embodiment of the present invention is identical to that of the first embodiment except for the following features. As shown in FIG. 18, an optical fiber bundle 4J is formed with a plurality of sub-bundles, in each of which a projection end of a first optical fiber 10J is disposed at a center of a rectangular pattern and four receiving ends of second optical fibers 20J are disposed at corners of the rectangular pattern. The sub-bundles are arranged on an end surface of the optical fiber bundle 4J such that two receiving ends of each of the sub-bundles is common with an adjacent sub-bundle.

In each of the sub-bundles, it is preferred that a center of a projection end of the first optical fiber 10J is at least separated from a center of an adjacent receiving end of the second optical fiber 20J by a distance L which is expressed by the following equation;

$$L = \{\sqrt{2} \times (d1 + d2)\}/2$$

wherein d1 is a diameter of the first optical fiber 10J, and d2 is a diameter of the second optical fiber 20J. In this embodiment, each of the first and second optical fibers (10J, 20J) has a diameter d of 200 μm. Therefore, the distance L is determined to be more than 280 μm, as calculated by the following equation;

$$L = \sqrt{2} \times d.$$

Figure 19:
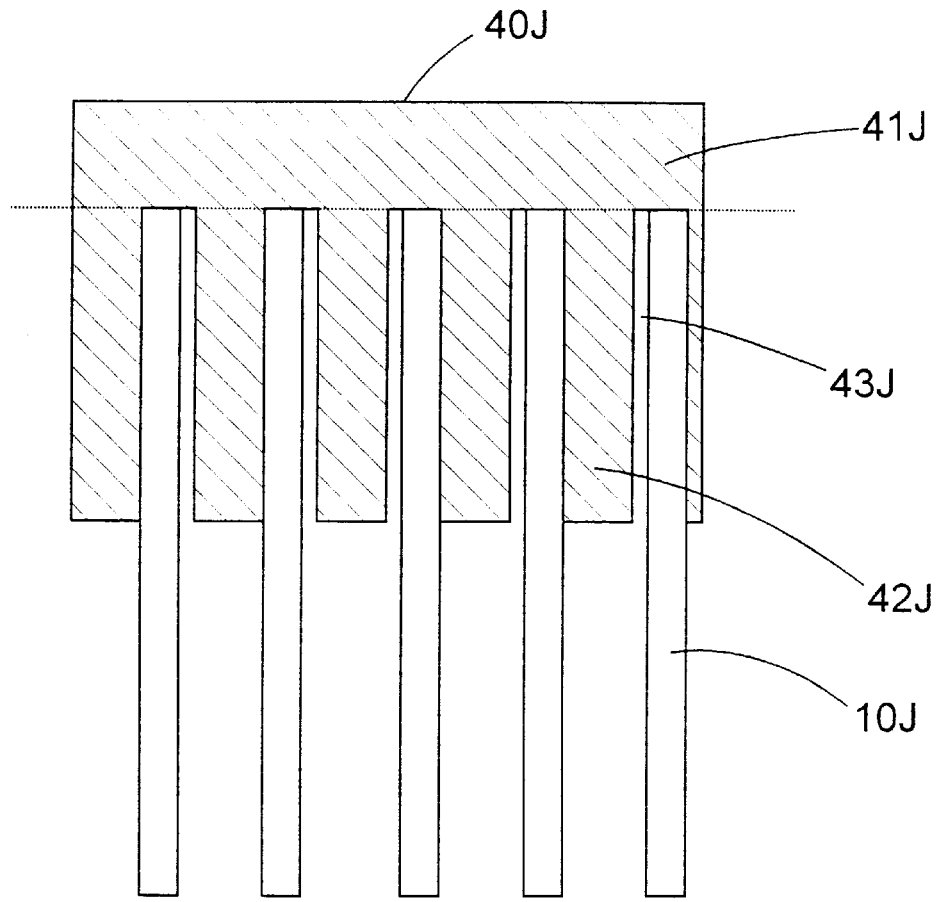
FIG. 19 is a cross-sectional view of a supporting member for supporting optical fibers used in the fifth embodiment.

To make this optical fiber bundle 4J, a plurality of supporting members 40J for supporting the first and second optical fibers (10J, 20J) are used. Each of the supporting members 40J is formed with a coupling portion 41J, a plurality of convex portions 42J, and grooves 43J formed between adjacent convex portions 42J, as shown in FIG. 19. The first and second optical fibers (10J, 20J) are disposed in the grooves 43J of the supporting members 40J. In this embodiment, a half of the supporting members 40J are used for the first optical fibers 10J, and the rest of the supporting members are used for the second optical fibers 20J.

Figure 20:
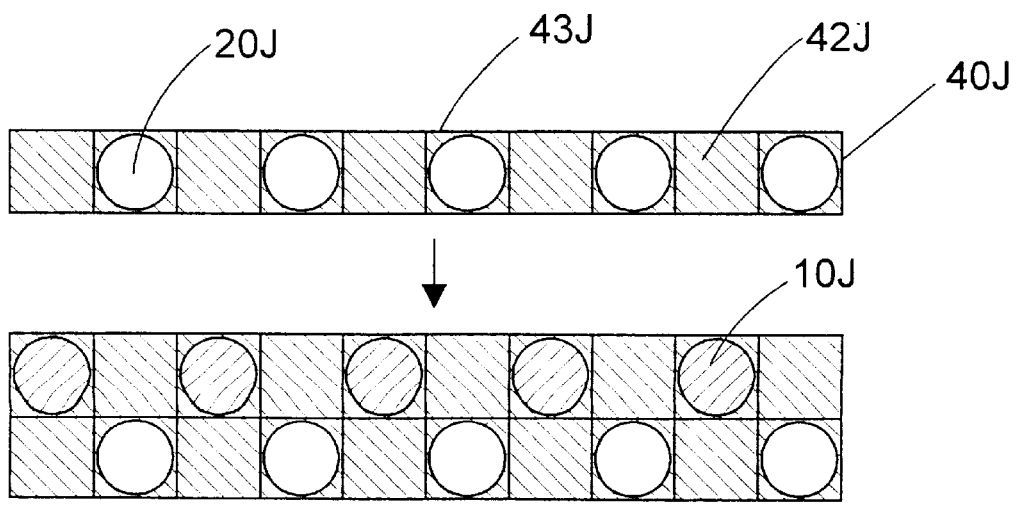
FIG. 20 shows a method of forming the optical fiber bundle of the fifth embodiment.

A method of forming the optical fiber bundle 4J comprises the steps of alternately stacking up the supporting members 40J mounting thereon the first optical fibers 10J and the supporting members mounting thereon the second optical fibers 20J, as shown in FIG. 20, bonding the supporting members each other, and cutting off the coupling portions of the supporting members along a dotted line of FIG. 19 to expose the projection ends and the receiving ends on the end surface of the optical fiber bundle 4J.

Figure 21:
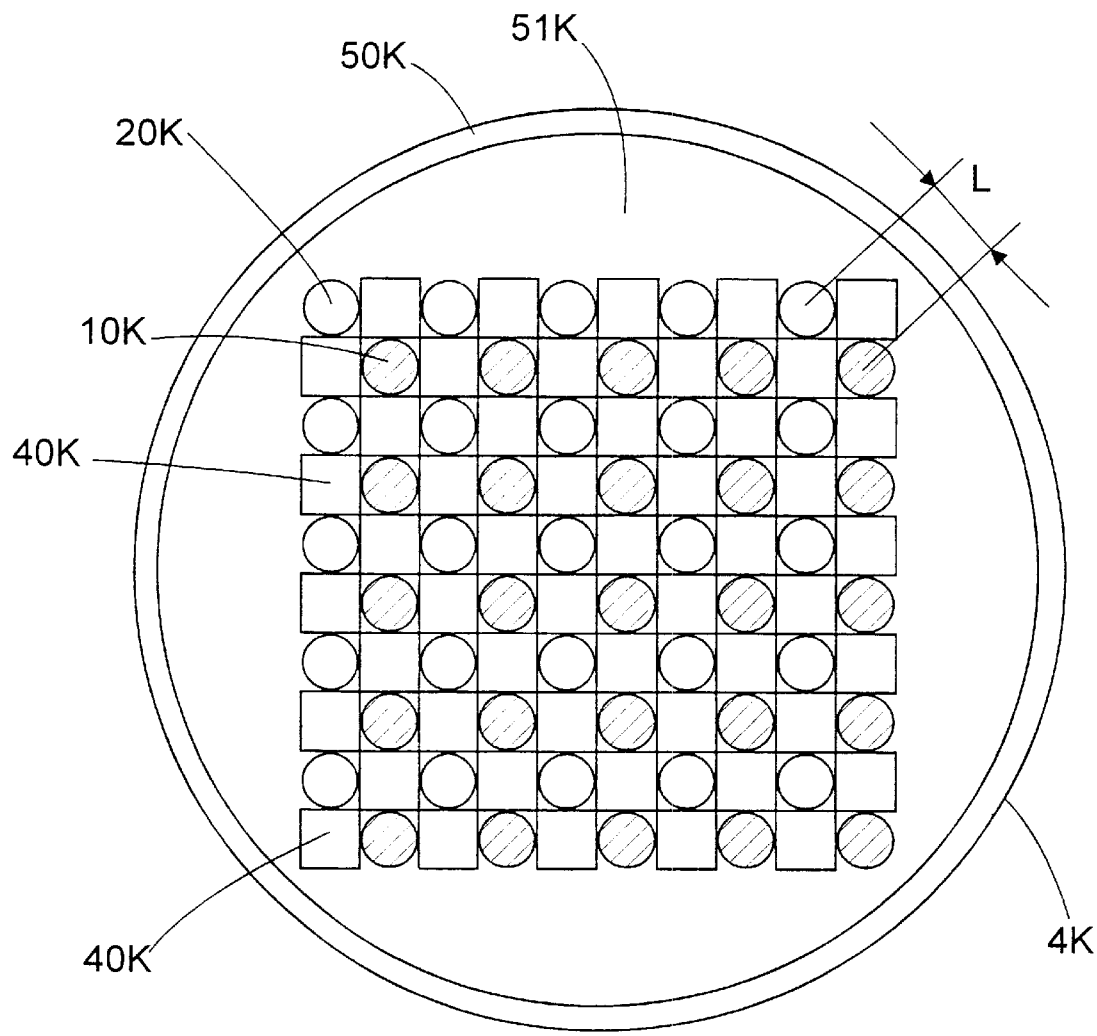
FIG. 21 is an end view of an optical fiber bundle of a first modification of the fifth embodiment.

As a first modification of the fifth embodiment, an optical fiber bundle 4K having first and second optical fibers (10K, 20K) arranged, as shown in FIG. 21, can be formed by the following method. Firstly, twenty five of the first optical fibers 10K each having a diameter of 200 μm, twenty five of the second optical fibers 20K each having a diameter of 200 μm, and fifty spacers 40K are prepared. Five first optical fibers 10K and five spacers 40K are alternately aligned, and then fixed each other to form a first sub-unit. This operation is repeated to obtain five first sub-units. Similarly, five second optical fibers 20K and five spacers 40K are alternately aligned, and then fixed each other to form a second sub-unit. This operation is repeated to obtain five second sub-units. Subsequently, the first and second sub-units are alternately stacked up, and bonded each other to obtain a fiber assembly. After the fiber assembly is disposed in a stainless tube 50K, an epoxy-resin adhesive 51K is supplied into the tube to obtain the optical fiber bundle 4K of this modification, as shown in FIG. 21. In this modification, a distance L between a center of each of the projection ends and a center of an adjacent receiving end is 280 μm.

Figure 22:
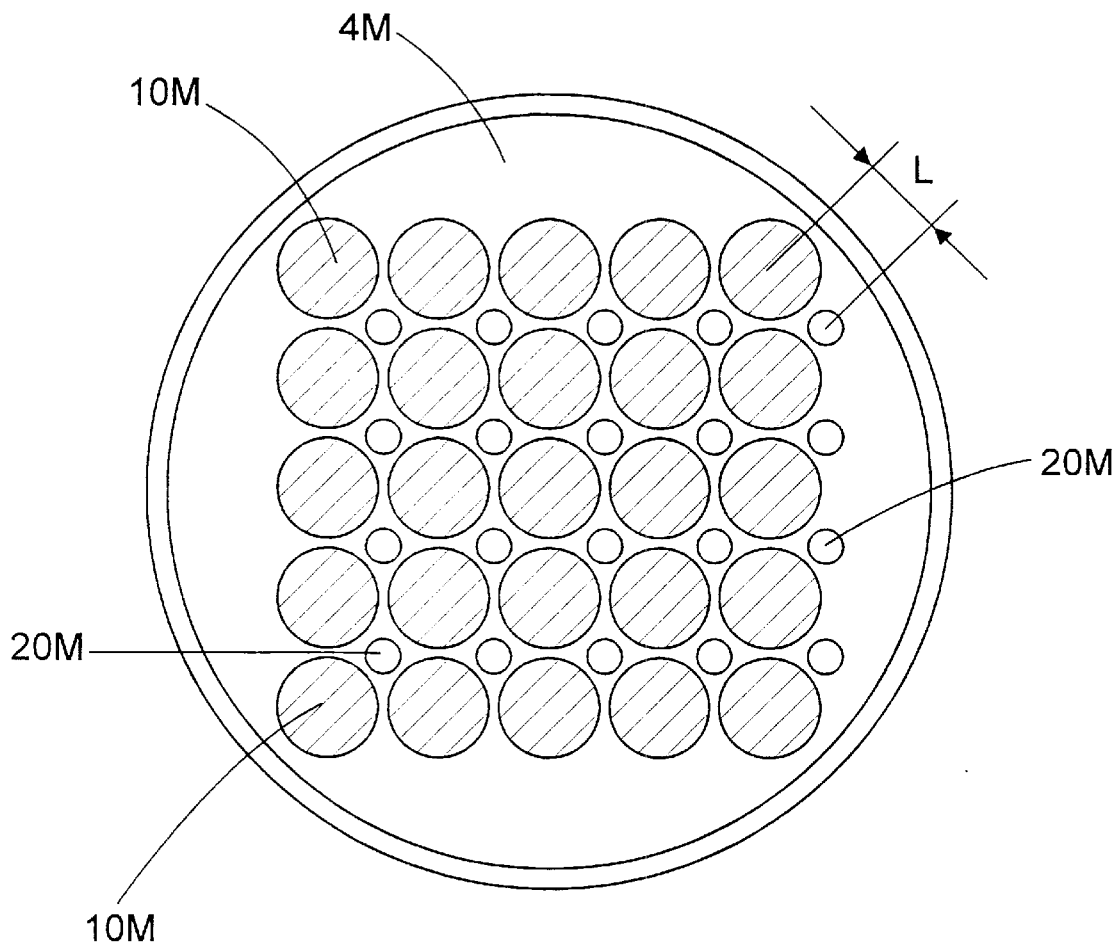
FIG. 22 is an end view of an optical fiber bundle of a second modification of the fifth embodiment.

As a second modification of the fifth embodiment, it is possible to use an optical fiber bundle 4M having first and second optical fibers (10M, 20M) arranged, as shown in FIG. 22. The optical fiber bundle 4M is formed with a plurality of sub-bundles, in each of which a projection end of the first optical fiber 10M is disposed on an end surface of the bundle at a center of a square pattern and four receiving ends of the second optical fibers 20M are disposed at corners of the square pattern. In this modification, diameters of the first and second optical fibers (10M, 20M) are 200 μm and 75 μm, respectively. A distance L between the projection end and an adjacent receiving end is adequately determined to fall within the range of 0.1 mm to 2 mm.

Sixth Embodiment

Figure 23:
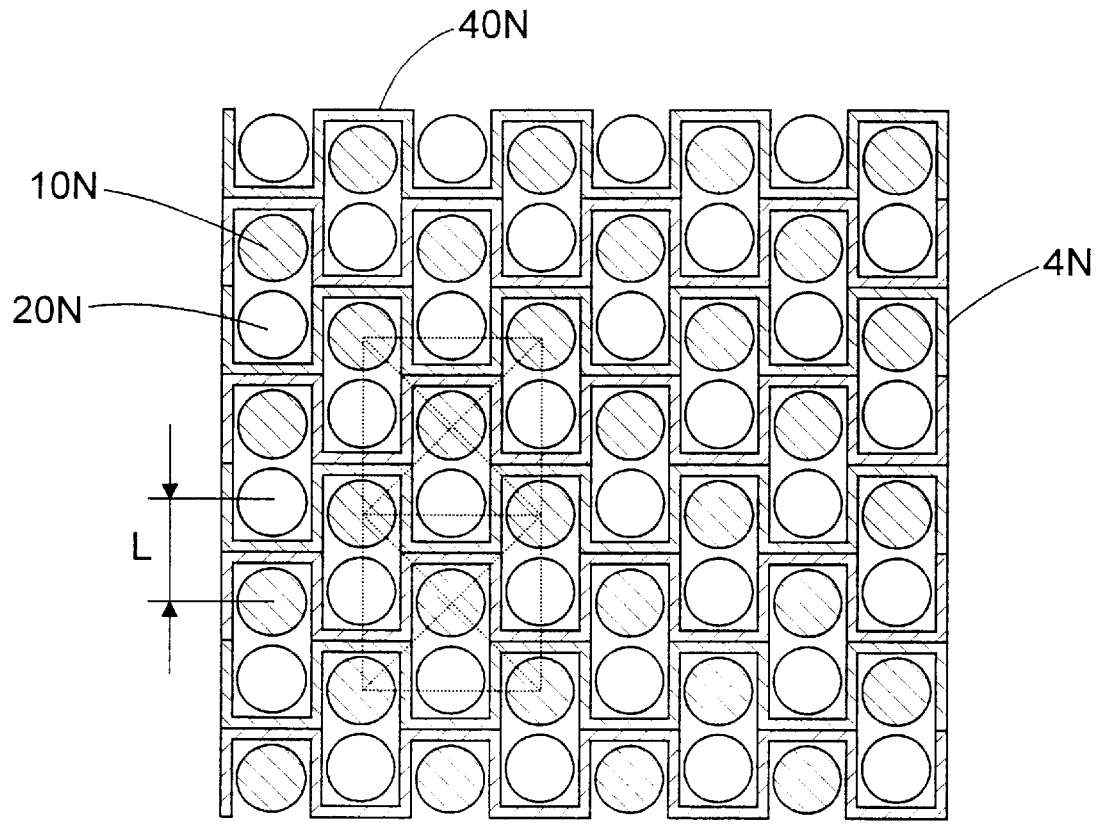
FIG. 23 is an end view of an optical fiber bundle of a sixth embodiment.

A device for non-invasive determination of a glucose concentration in the blood of a subject of a sixth embodiment of the present invention is identical to that of the first embodiment except for the following features. As shown in FIG. 23, an optical fiber bundle 4N is formed with a plurality of sub-bundles, in each of which five projection ends of first optical fibers 10N are disposed on an end surface of the bundle at a center of a square pattern and four corners of the square pattern, and four receiving ends of second optical fibers 20N are disposed on four sides of the square pattern between adjacent projection ends. The sub-bundles are arranged on the end surface of the optical fiber bundle 4N such that one receiving end and two projection ends of each of the sub-bundles are common with an adjacent sub-bundle. A distance L between a projection end and an adjacent receiving end is adequately determined to fall within the range of 0.1 mm to 2 mm.

To make this optical fiber bundle 4N, a plurality of supporting members 40N for supporting the first and second optical fibers (10N, 20N) are used. Each of the supporting members 40N is formed with first grooves 41N having openings at its bottom surface and second grooves 42N having openings at its top surface. The first and second optical fibers (10N, 20N) are respectively disposed in the first and second grooves (41N, 42N) such that projection and receiving ends thereof are alternately aligned.

Figure 24:
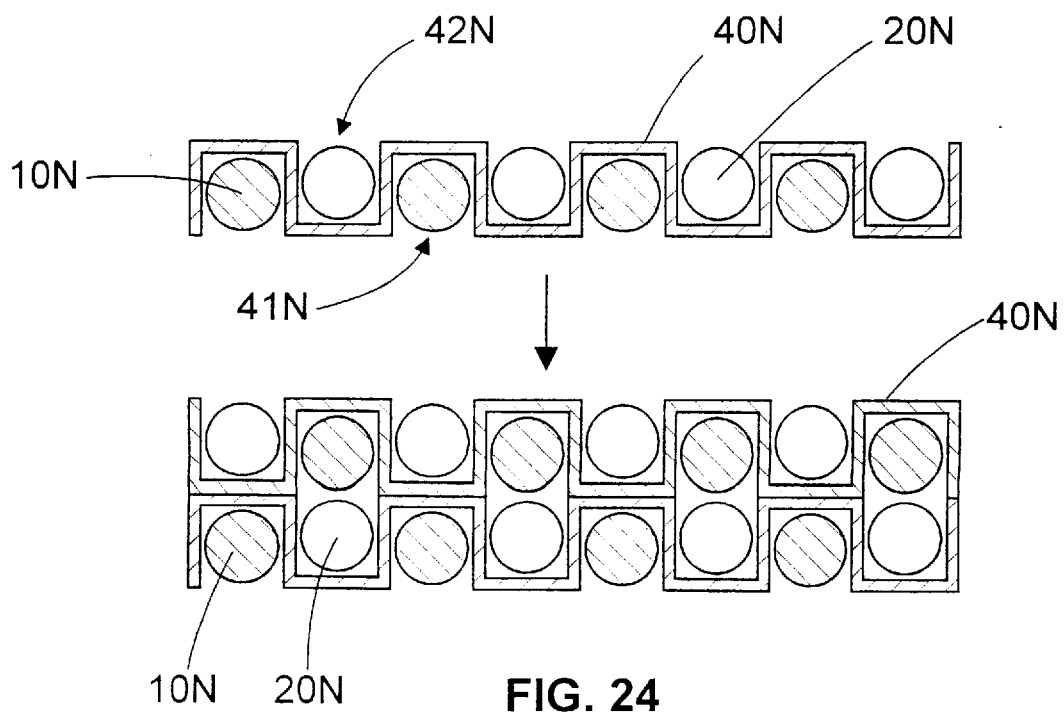
FIG. 24 shows a method of forming the optical fiber bundle of the sixth embodiment.

A method of forming the optical fiber bundle 4N comprises the steps of stacking up the supporting members 40N such that the projection ends of the first optical fibers 10N are disposed adjacent to the receiving ends of the second optical fibers 20N in a stacking direction, as shown in FIG. 24, and bonding the supporting members each other to obtain the optical fiber bundle 4N. This embodiment presents an advantage that a distance between each of the projection ends and an adjacent receiving end can be determined by changing a thickness of the supporting member 40N.

Figure 25:
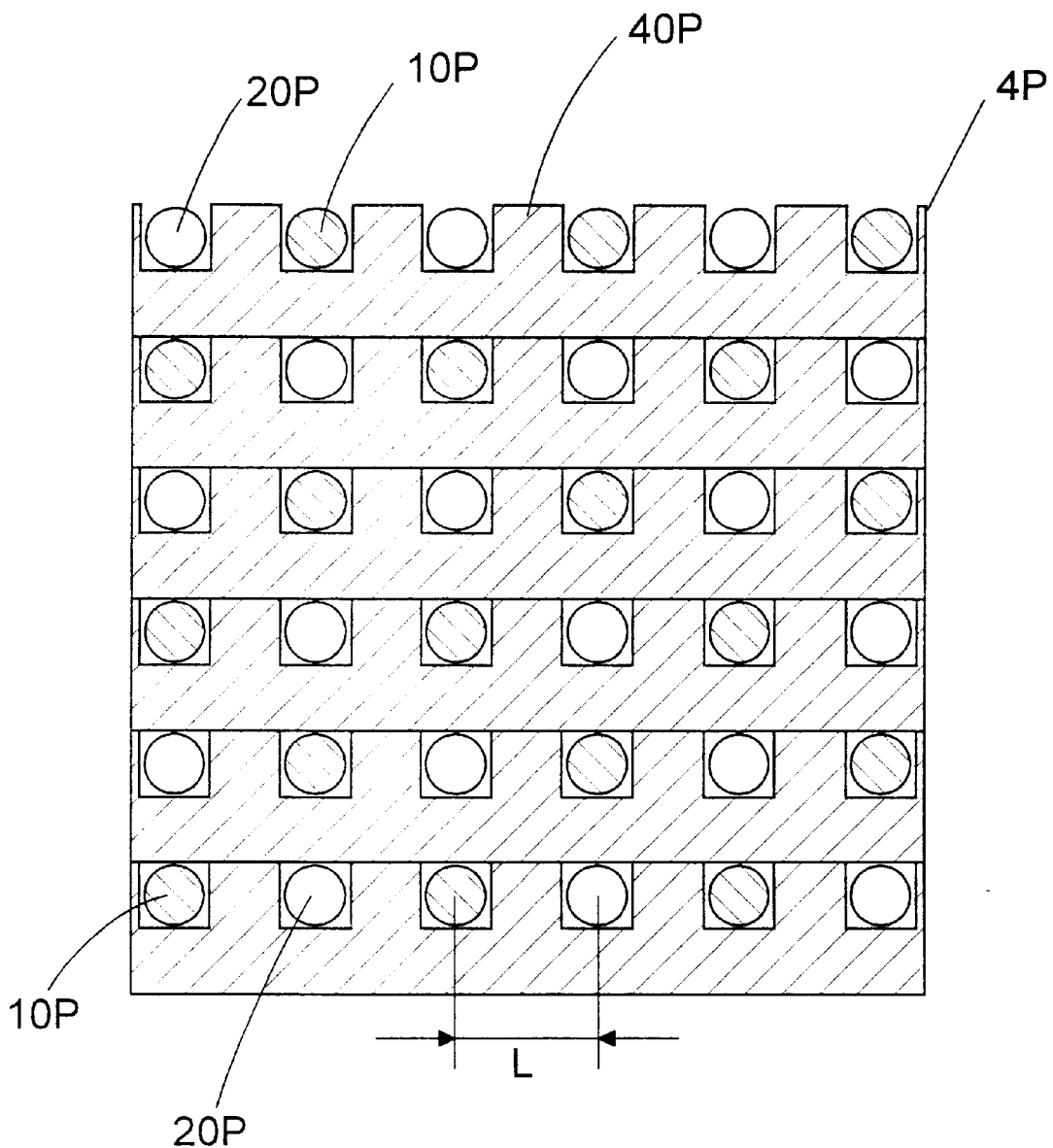
FIG. 25 is an end view of an optical fiber bundle of a first modification of the sixth embodiment.
Figure 26:
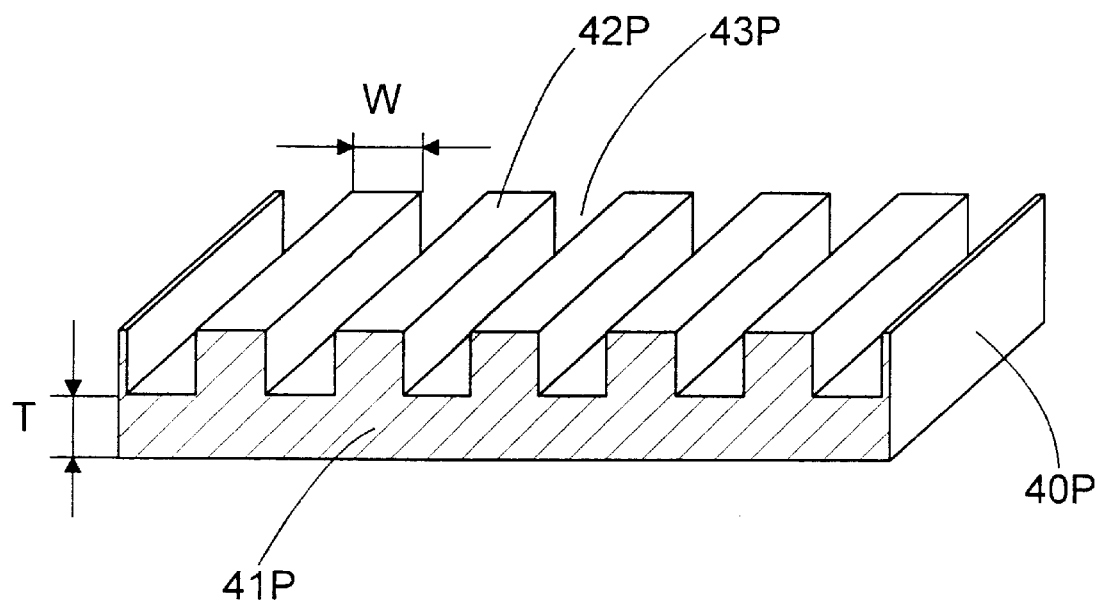
FIG. 26 is a perspective view of a supporting member for supporting optical fibers used in the first modification of the sixth embodiment.
Figure 27:
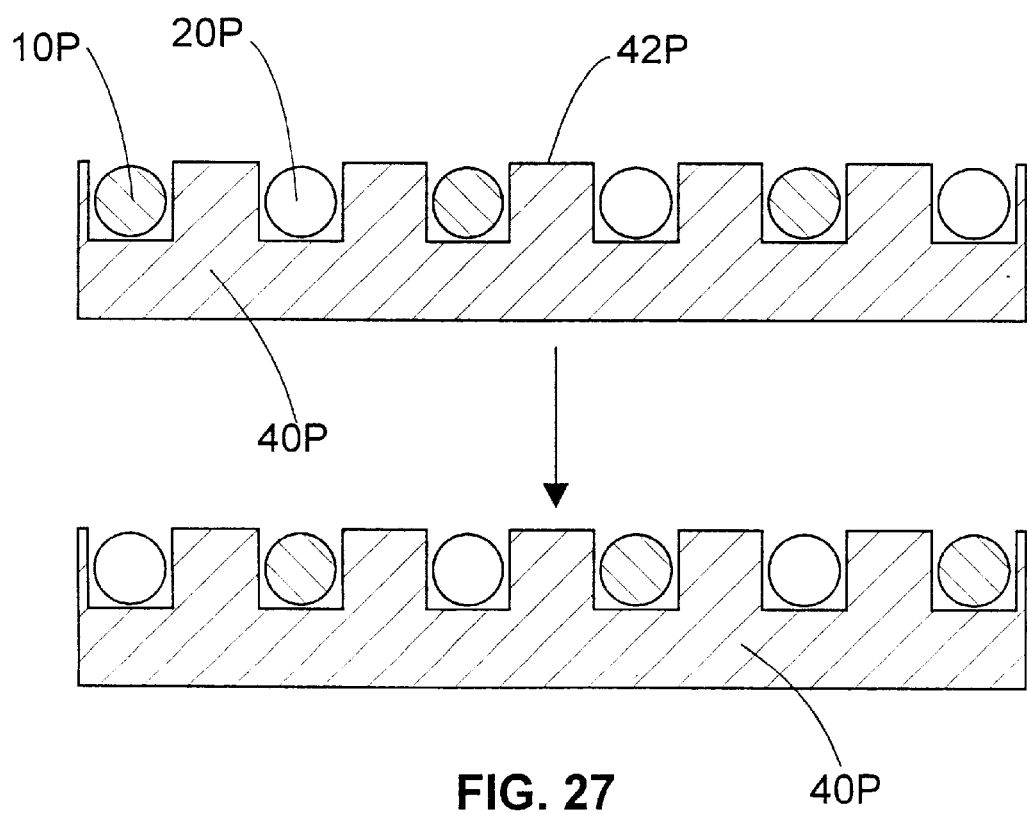
FIG. 27 shows a method of forming the optical fiber bundle of the first modification of the sixth embodiment.

As a first modification of the sixth embodiment, an optical fiber bundle 4P having first and second optical fibers (10P, 20P) arranged, as shown in FIG. 25, can be formed by the following method. That is, a plurality of supporting members 40P for supporting the first and second optical fibers (10P, 20P) are prepared. Each of the supporting members 40P has a coupling portion 41P, a plurality of convex portions 42P, and grooves 43P formed between adjacent convex portions 42P, as shown in FIG. 26. The first and second optical fibers (10P, 20P) are alternately arranged in the grooves 43P of the supporting members 40P. The supporting members 40P mounting thereon the first and second optical fibers (10P, 20P) are stacked up such that projection ends of the first optical fibers are disposed adjacent to receiving ends of the second optical fibers in a stacking direction, as shown in FIG. 27, and then fixed each other to obtain the optical fiber bundle 4P of this modification. In this embodiment, each of the first and second optical fibers (10P, 20P) has a diameter of 200 μm. A thickness T of the coupling portion 41P and a width W of the convex portions 42P are 200 μm. Therefore, a distance L between a center of each of the projection ends and a center of an adjacent receiving end is 400 μm.

Figure 28:
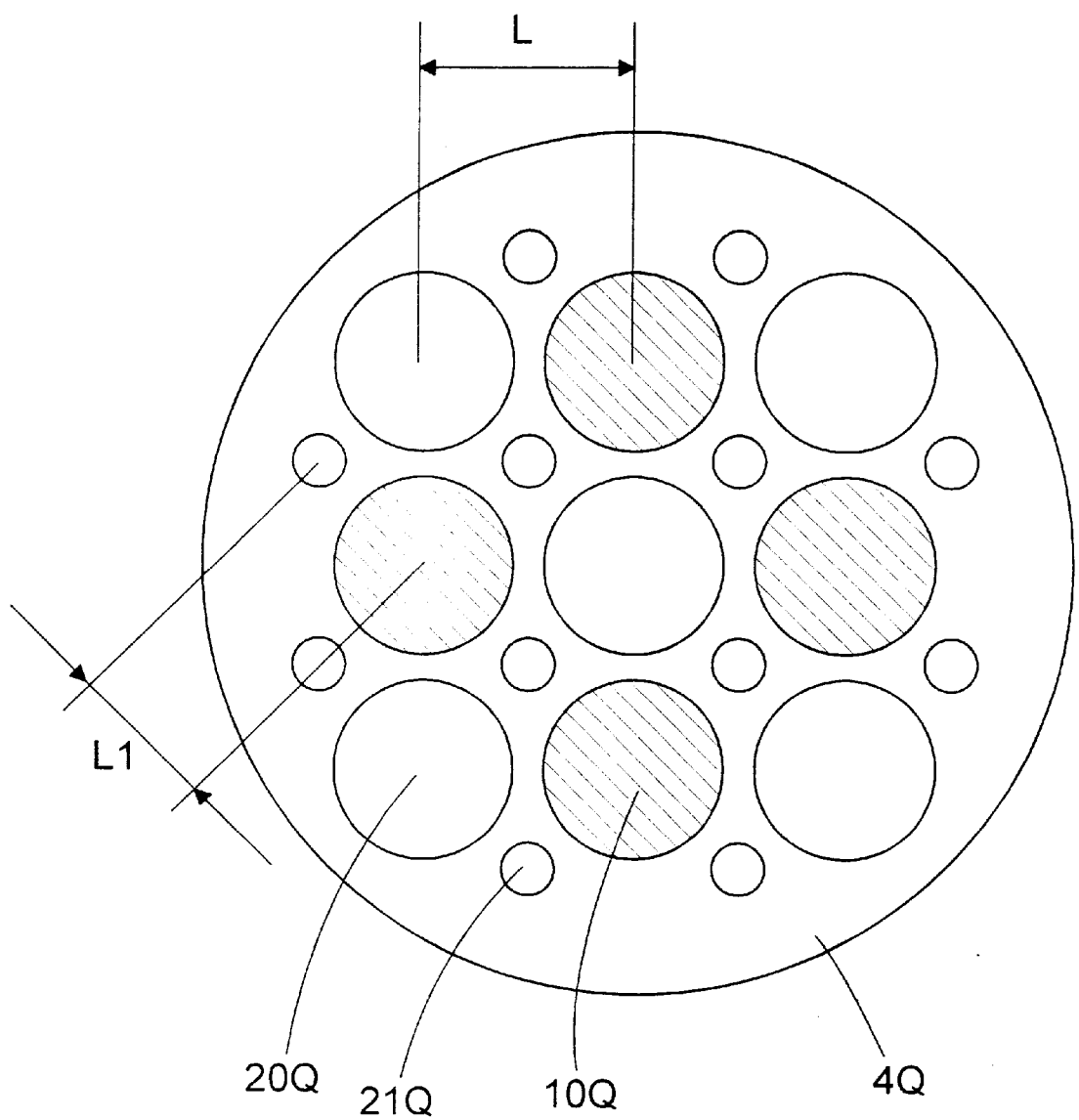
FIG. 28 is an end view of an optical fiber bundle of a second modification of the sixth embodiment.

As a second modification of the sixth embodiment, it is possible to use an optical fiber bundle 4Q, as shown in FIG. 28. The optical fiber bundle 4Q is formed with receiving ends of second optical fibers 20Q disposed on an end surface of the bundle at a center and four corners of a square pattern, and projection ends of first optical fibers 10Q disposed on four sides of the square pattern between adjacent receiving ends. Each of the first and second optical fibers (10Q, 20Q) has a diameter of 500 μm. In addition, the optical fiber bundle 4Q comprises twelve supplemental second optical fibers 21Q each having a diameter of 250 μm. Four supplemental second optical fibers 21Q are arranged around each of the first optical fibers 10Q, as shown in FIG. 28. A distance L between a projection end and a receiving end of the second optical fiber 20Q, and a distance L1 between the projection end and an adjacent receiving end of the supplemental second optical fiber 21Q are adequately determined to fall within the range of 0.1 mm to 2 mm such that the distance L is larger than the distance L1.

Seventh Embodiment

Figure 29:
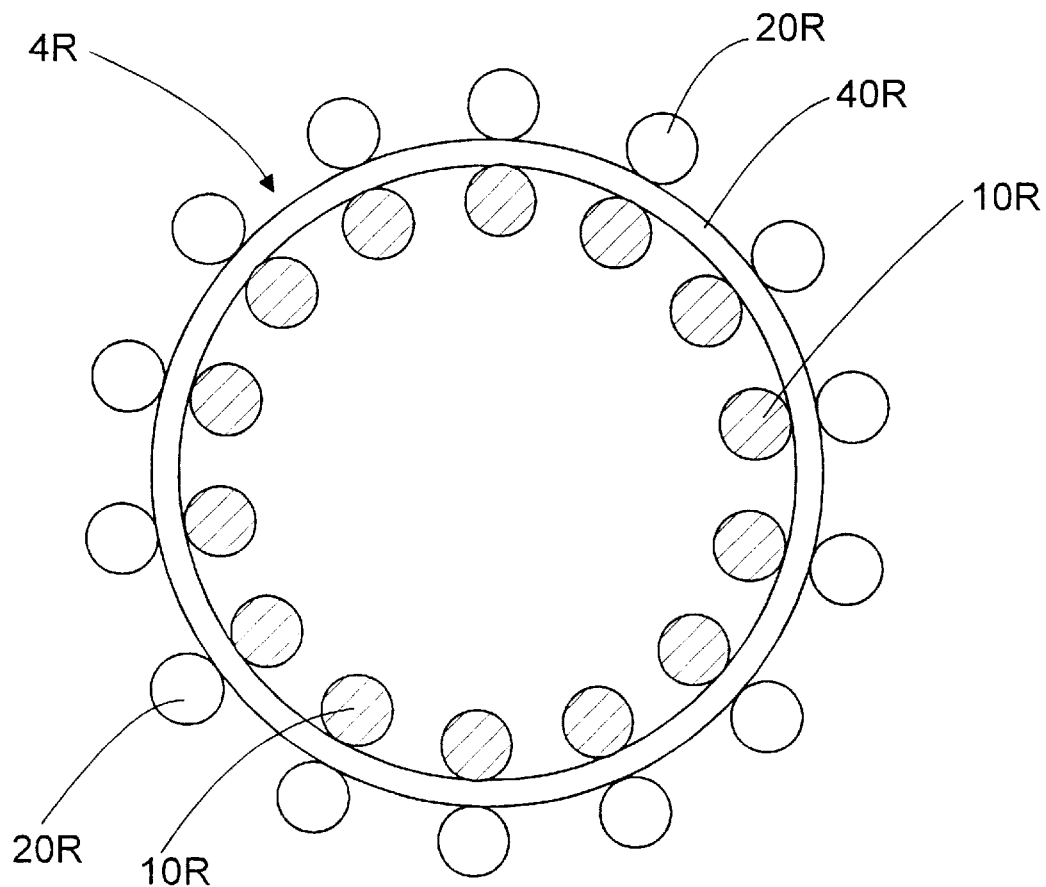
FIG. 29 is an end view of an optical fiber bundle of a seventh embodiment.

A device for non-invasive determination of a glucose concentration in the blood of a subject of a seventh embodiment of the present invention is identical to that of the first embodiment except for a structure of an optical fiber bundle 4R. That is, as shown in FIG. 29, the optical fiber bundle 4R is formed with a plurality of first optical fibers 10R of which projection ends are disposed on an end surface of the bundle along a circular pattern and inside of the circular pattern, and a plurality of second optical fibers 20R of which receiving ends are disposed along the circular pattern and outside of the circular pattern.

Figure 30:
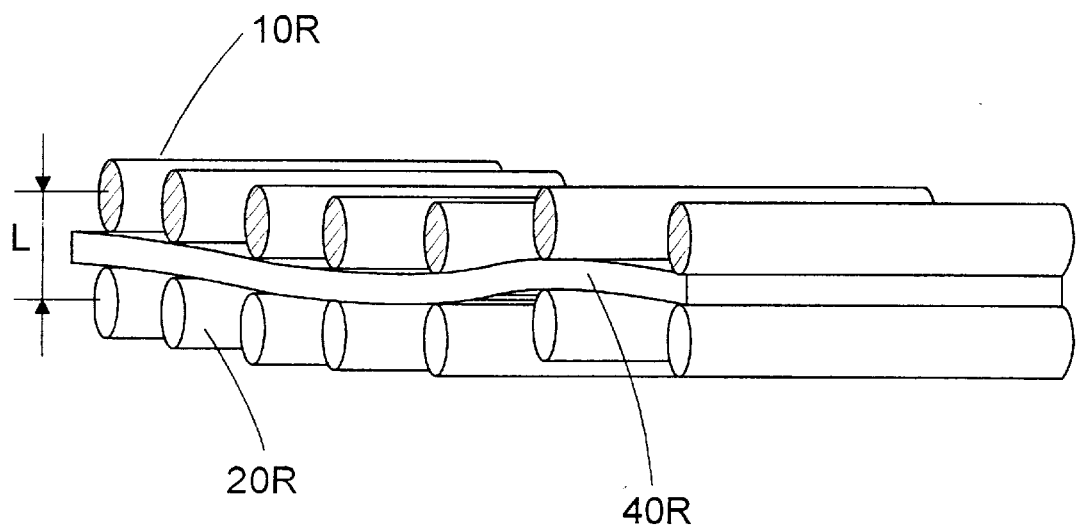
FIG. 30 is a perspective view of a spacer sheet mounting thereon first and second optical fibers.

For example, the optical fiber bundle 4R can be formed by the following method. The first optical fibers 10R are fixed on a surface of a spacer sheet 40R by a predetermined interval, and then the second optical fibers 20R are fixed on the opposite surface of the spacer sheet by the predetermined interval such that each of the receiving ends is positioned just below an adjacent projection end through the spacer sheet, as shown in FIG. 30. The optical fiber bundle 4R is obtained by making a tube with the spacer sheet 40R mounting thereon the first and second optical fibers (10R, 20R), as shown in FIG. 29. Alternatively, it is possible to form an optical fiber bundle (not shown) by winding the spacer sheet 40R in a spiral configuration.

In this embodiment, each of the first and second optical fibers (10R, 20R) has a diameter of 200 μm, and a thickness of the spacer sheet 40R is 100 μm. Therefore, a distance L between each of the projection ends and the adjacent receiving end is 300 μm. Thus, there is an advantage that the distance L can be selected by changing a thickness of the spacer sheet 40R.

Figure 31:
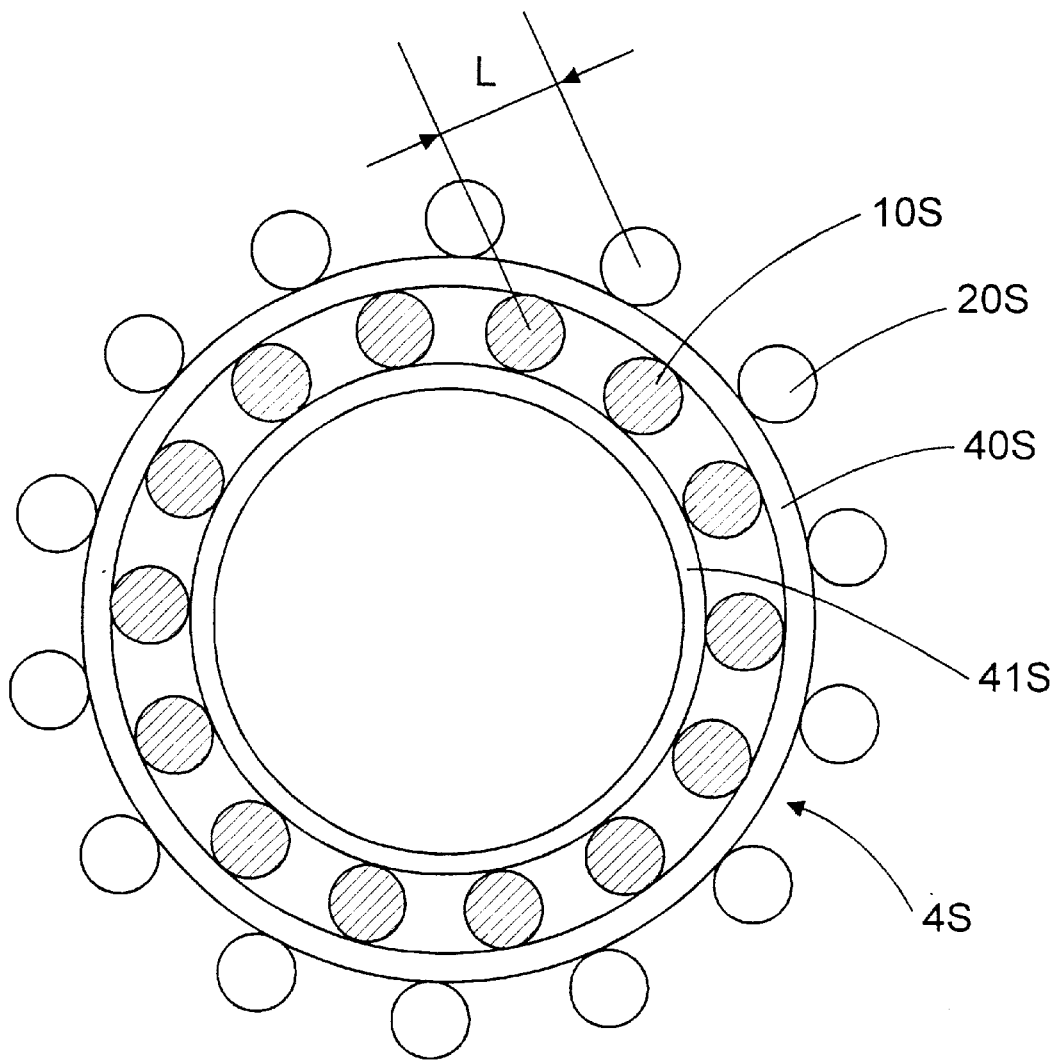
FIG. 31 is an end view of an optical fiber bundle of a first embodiment of the seventh embodiment.

As a modification of the seventh embodiment, it is possible to use an optical fiber bundle 4S, as shown in FIG. 31. That is, the optical fiber bundle 4S differs from the optical fiber bundle 4R in that each of receiving ends of second optical fibers 20S is not positioned just below an adjacent projection end of a first optical fiber 10S through a spacer tube 40S. A distance L between each of the projection ends and the adjacent receiving end is adequately determined to fall within the range of 0.1 mm to 2 mm.

Figure 32:
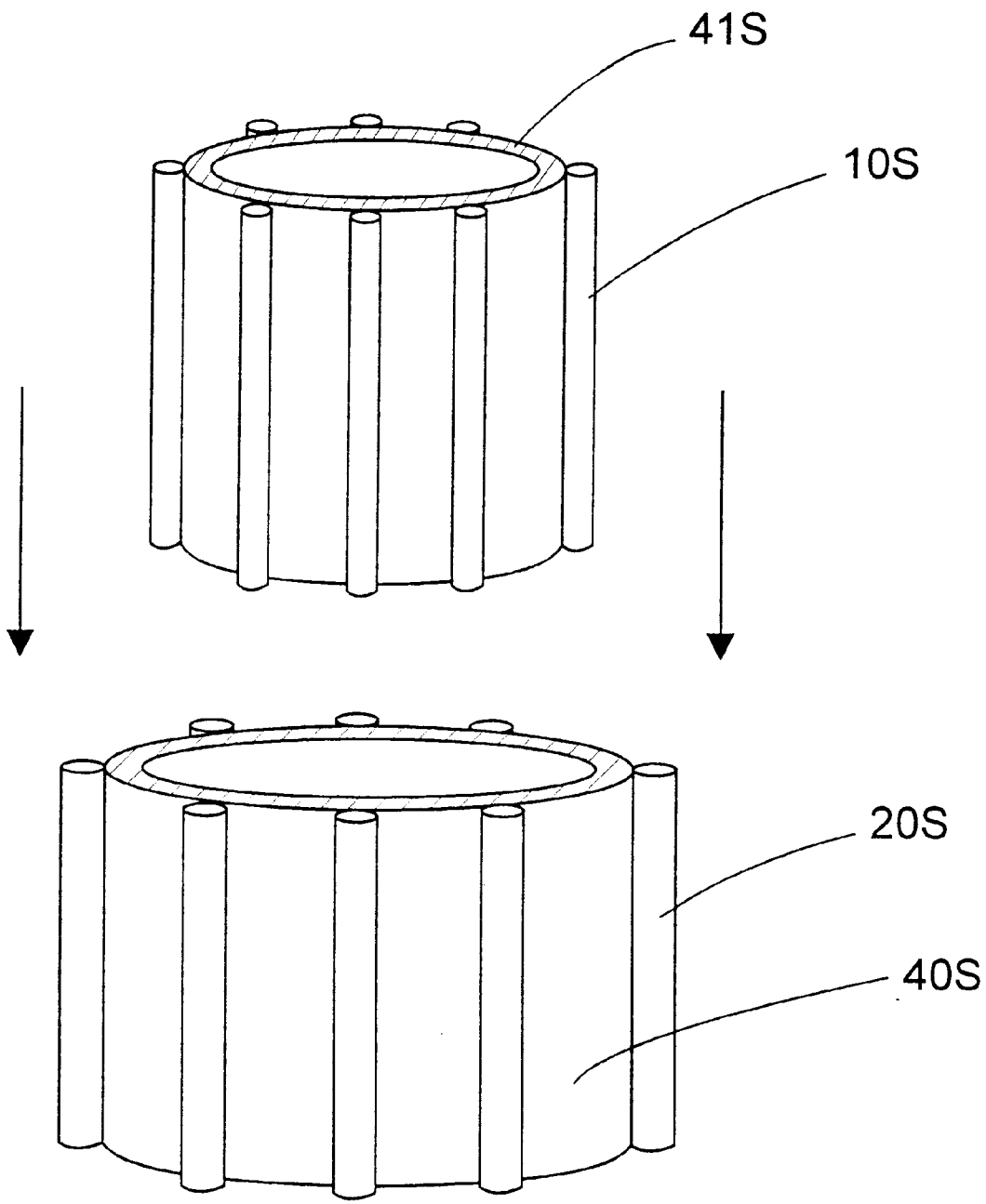
FIG. 32 shows a method of forming the optical fiber bundle of the first modification of the seventh embodiment.

This optical fiber bundle 4S can be formed by the following method. Spacer tubes (40S, 41S) having different diameters are prepared. The first optical fibers 10S are fixed on an outer surface of the spacer tube 41S along an axial direction of the tube by a predetermined interval. Similarly, the second optical fibers 20S are fixed on an outer surface of the spacer tube 40S along an axial direction of the tube by the predetermined interval. Then, the spacer tube 41S is inserted into the spacer tube 40S such that the first optical fibers 10S on the spacer tube 41S contact an inner surface of the spacer tube 40S, as shown in FIG. 32, and then fixed to the spacer tube 40S to obtain the optical fiber bundle 4S.

Eight Embodiment

Figure 33:
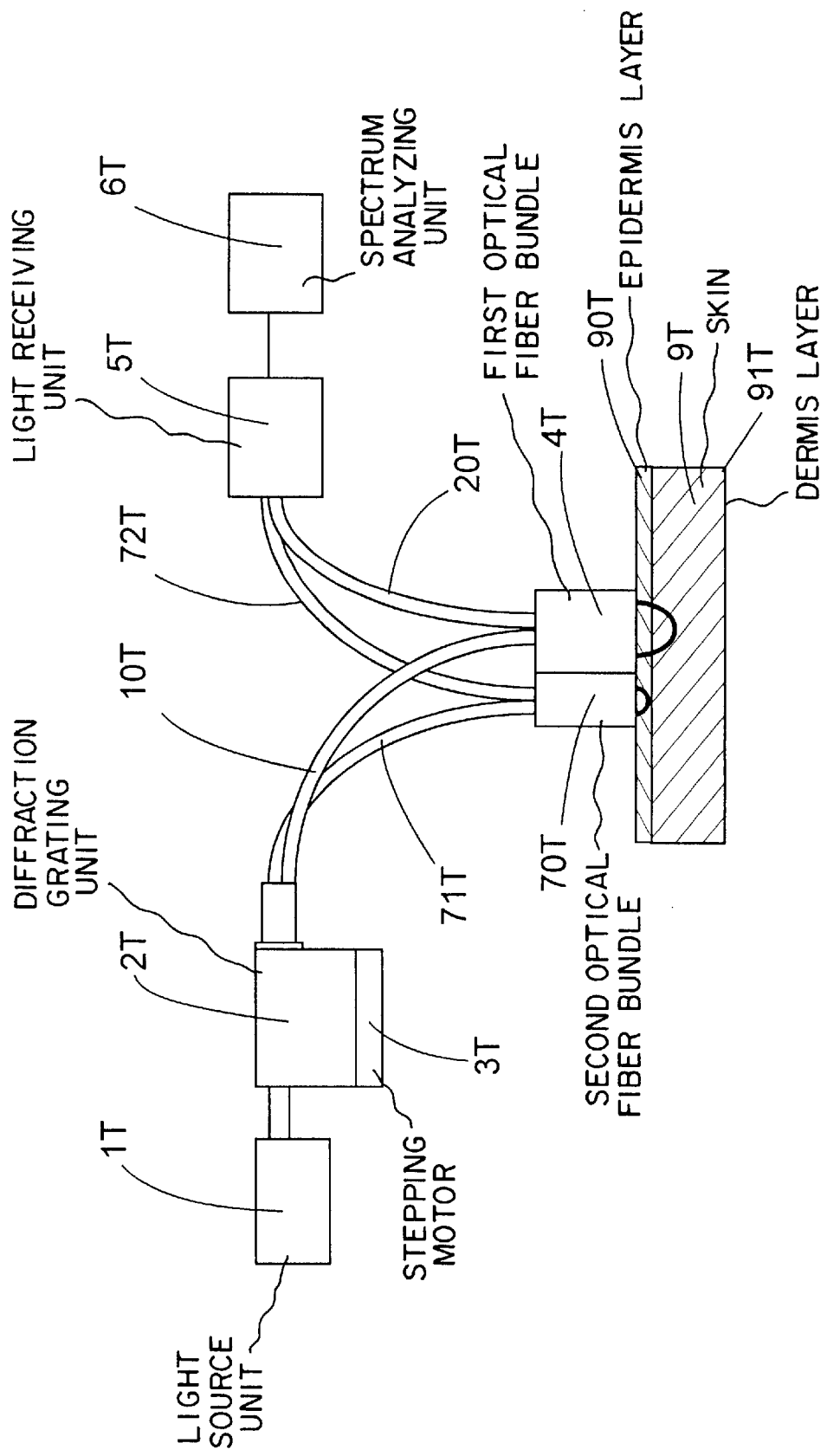
FIG. 33 is a schematic diagram of a device for non-invasive determination of a glucose concentration in the blood of a subject of an eighth embodiment of the present invention.

A device for non-invasive determination of a glucose concentration in the blood of a subject of an eighth embodiment of the present invention is identical to that of the first embodiment except that a first optical fiber bundle 4T and a second optical fiber bundle 70T are used, as shown in FIG. 33. Therefore, no duplicate explanation to common parts and operation is deemed necessary.

Figure 34:
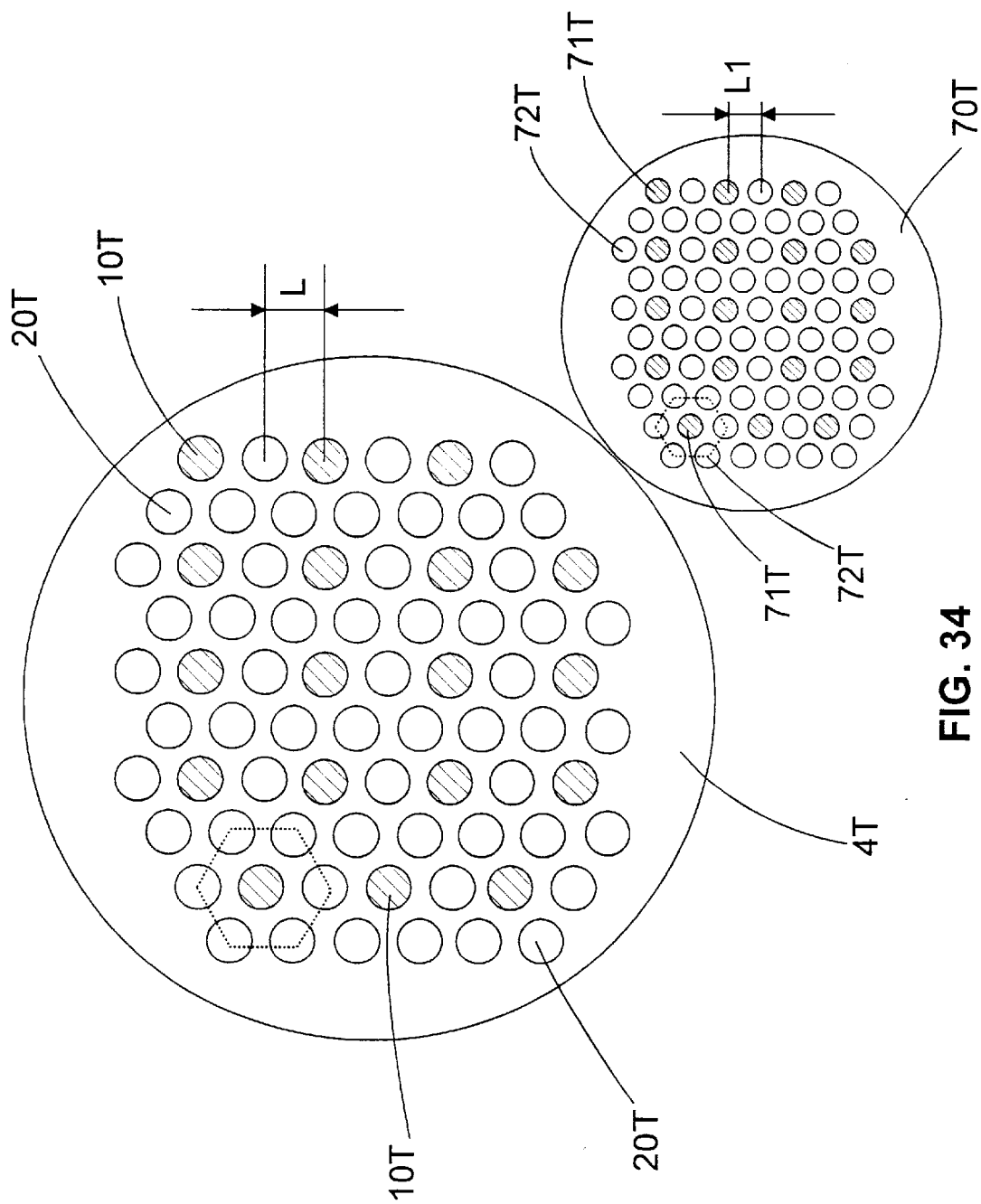
FIG. 34 is an end view of an optical fiber bundle of the eighth embodiment.

As shown in FIG. 34, the first bundle 4T is formed with a plurality of sub-bundles, in each of which a projection end of a first optical fiber 10T is disposed on an end surface of the first bundle at a center of a hexagonal pattern, and six receiving ends of second optical fibers 20T are disposed at corners of the hexagonal pattern. Each of the first and second optical fibers (10T, 20T) has a diameter of 500 μm. A distance L between each of the projection ends and an adjacent receiving end is determined to fall within the range of 0.1 mm to 2 mm such that the receiving end can selectively sense the resulting radiation emitted from a dermis layer 91T of a skin 9T of the subject.

On the other hand, the second bundle 70T is formed with a plurality of sub-bundles, in each of which a projection end of a third optical fiber 71T is disposed on an end surface of the second bundle at a center of a hexagonal pattern, and six receiving ends of fourth optical fibers 72T are disposed at corners of the hexagonal pattern. The third optical fibers 71T are connected at the opposite ends to a light source unit, and the fourth optical fibers 72T are connected at the opposite ends to a light receiving unit 5T, as shown in FIG. 33. Each of the third and fourth optical fibers (71T, 72T) has a diameter of 250 μm. In the second bundle 70T, a distance L1 between each of the projection ends and an adjacent receiving end is determined such that the receiving end can selectively sense the resulting radiation emitted from an epidermis layer 90T of the skin 9T.

By using a subtraction between adsorption spectra obtained through the first and second bundles (4T, 70T), it is possible to provide an adsorption spectrum of only the dermis layer 91T.

Ninth Embodiment

Figure 35:
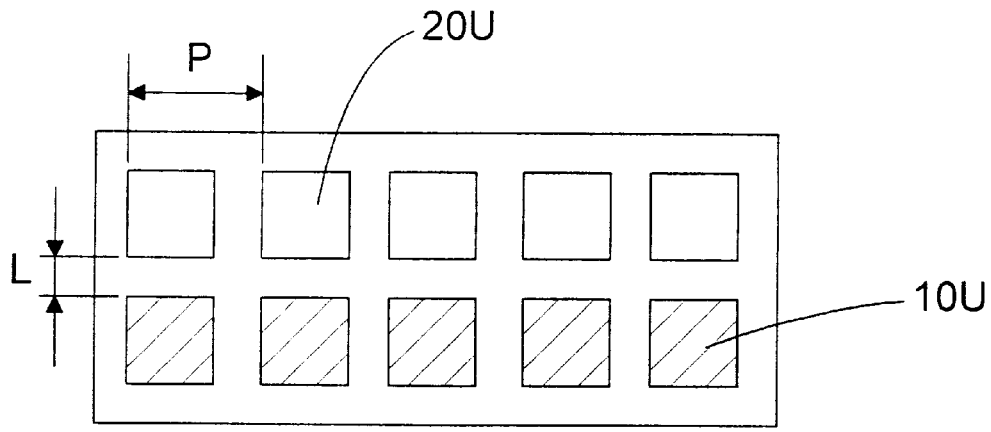
FIG. 35 is an end view of an optical fiber bundle of a ninth embodiment.

A device for non-invasive determination of a glucose concentration in the blood of a subject of a ninth embodiment of the present invention is identical to that of the first embodiment except that a plurality of luminescent semiconductor diodes 10U are used in place of the first optical fibers 10, and receiving elements 20U are used in place of the second optical fibers 20. Each of the diodes 10U and the receiving elements 20U is of a square shape of 100 μm×100 μm. Five diodes 10U are aligned by a pitch P of 200 μm to obtain a diode array. Five receiving elements 20U are aligned by the pitch P of 200 gm to obtain a receiving element array. As shown in FIG. 35, the diode array is separated from the receiving element array by a distance L of 100 μm.

Tenth Embodiment

Figure 36:
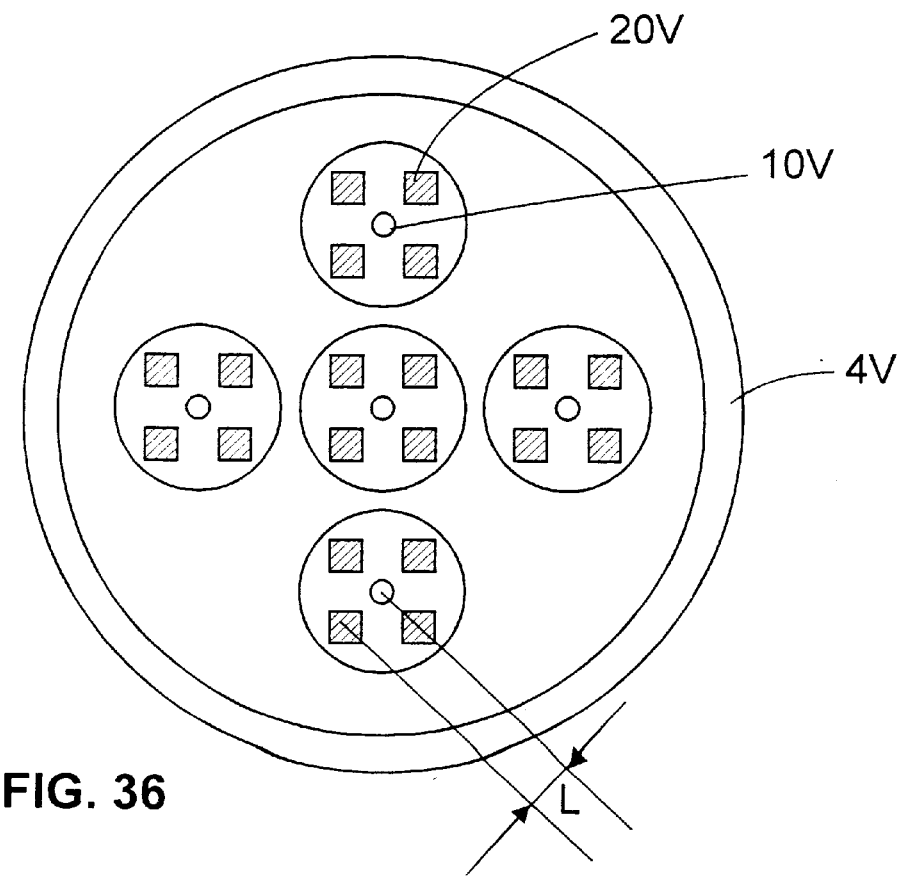
FIG. 36 is an end view of an optical fiber bundle of a tenth embodiment.

A device for non-invasive determination of a glucose concentration in the blood of a subject of a tenth embodiment of the present invention is identical to that of the first embodiment except that receiving elements 20V are used in place of the second optical fibers 20. As shown in FIG. 36, an optical fiber bundle 4V is formed with five sub-bundles, each of which is composed of four receiving elements 20V disposed on an end surface of the bundle at corners of a square pattern and a projection end of a first optical fiber 10V disposed on the end surface at a center of the square pattern. A distance L between a center of the projection end and a center of an adjacent receiving element 20V is determined to fall within the range of 0.1 mm to 2 mm.

Eleventh Embodiment

Figure 37:
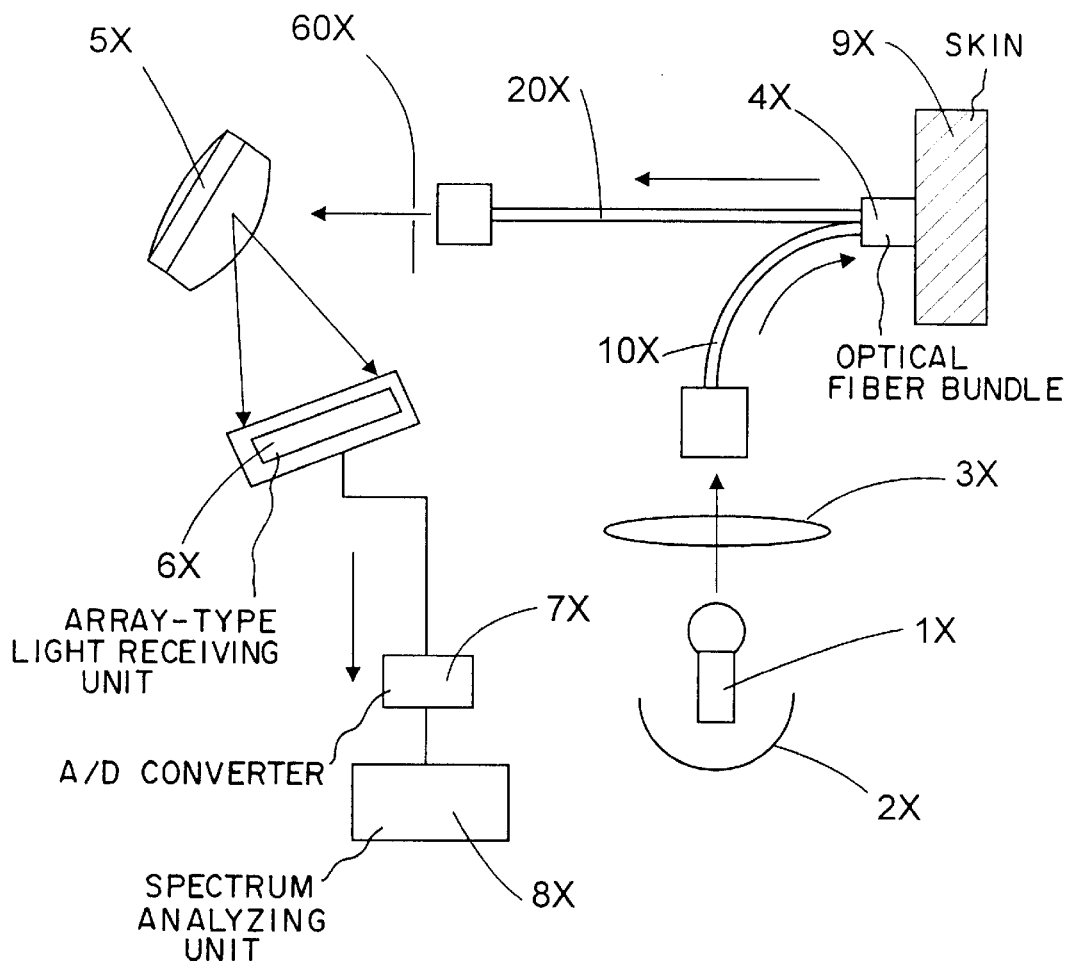
FIG. 37 is a schematic diagram of a device for non-invasive determination of a glucose concentration in the blood of a subject of an eleventh embodiment of the present invention.
Figure 38:
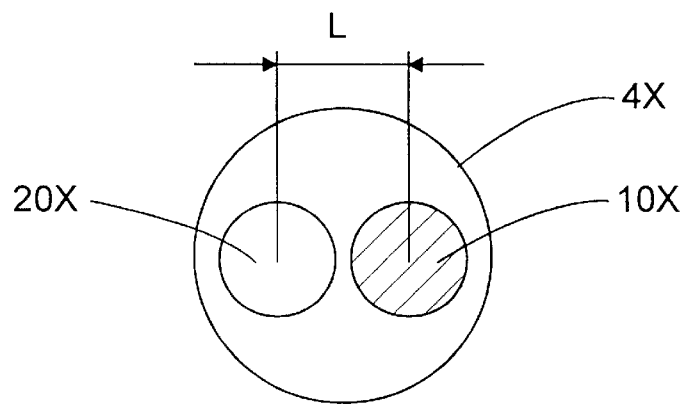
FIG. 38 is an end view of an optical fiber bundle of the eleventh embodiment.
Figure 39:
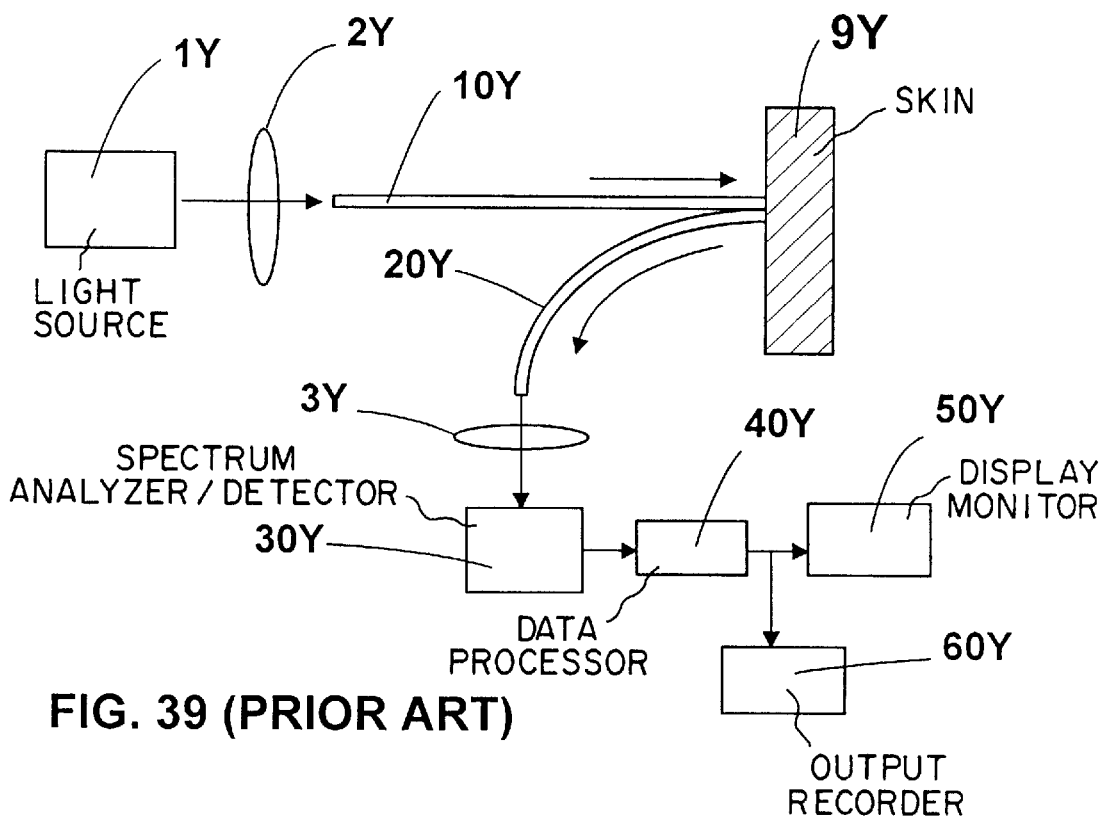
FIG. 39 is a schematic diagram of a device for non-invasive determination of a glucose concentration in the blood of a patient of the prior art.
Figure 40:
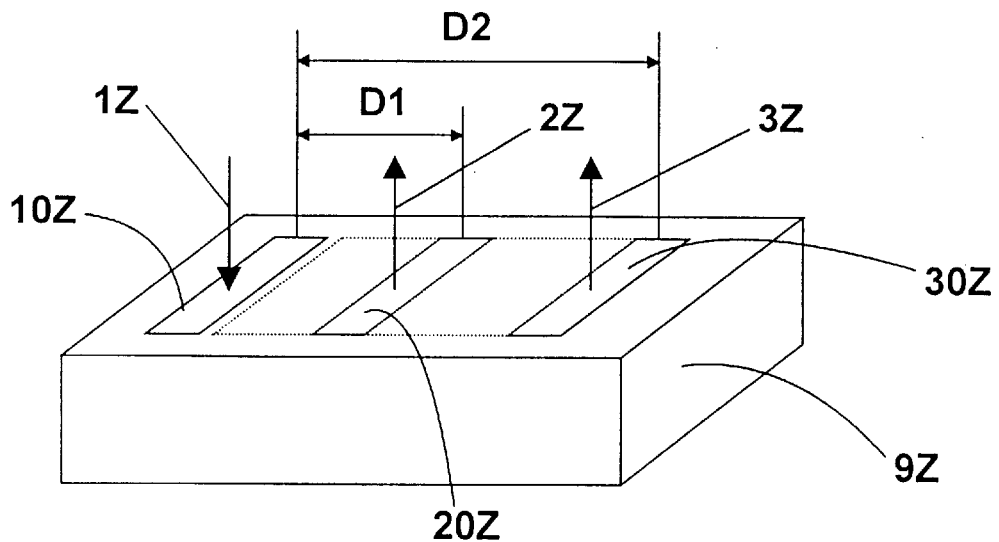
FIG. 40 is a schematic diagram illustrating a method for determining a glucose concentration in a biological matrix of the prior art.

A device for non-invasive determination of a glucose concentration in the blood of a subject of an eleventh embodiment of is the present invention is explained below. That is, as shown in FIG. 37, a light source unit comprises a halogen lamp 1X of about 150 W having a reflection mirror 2X, and a first lens system 3X disposed between the halogen lamp and a first optical fiber 10X. An optical fiber bundle 4X is formed with the first optical fiber 10X having a diameter of 750 μm for projecting near-infrared radiation on a skin 9X of the subject and a second optical fiber 20X having a diameter of 750 μm for receiving a resulting radiation emitted from the inside of the skin. A projection end of the first optical fiber 10X and a receiving end of the second optical fiber 20X are exposed at an end surface of the bundle 4X, as shown in FIG. 38. A distance L between the projection end and the receiving end is determined to fall within the range of 0.1 mm to 2 mm.

The resulting radiation received by the second optical fiber 20X is introduced through a slit 60X into a flat-field type diffraction grating unit 5X as a spectroscope of the resulting radiation, and then sent to an array-type light receiving unit 6X of 256 photo-diodes made of In-Ga-As and having a wavelength-sensitivity of 0.9 μm to 2.1 μm, which is cooled by the use of Peltier elements (not shown). In FIG. 37, numeral 7X designates an A/D converter disposed between the light receiving unit 6X and a spectrum analyzing unit 8X comprising a microcomputer.

In the spectrum analyzing unit 8X, a spectrum analysis of the resulting radiation provided by the second optical fiber 20X is made, and then a multivariate analysis is performed by the use of an adsorption spectrum of near-infrared radiation of 1.4 μm to 1.8 μm to determine the glucose concentration in the blood of the subject.

As a modification, it would be possible to use an optical fiber bundle of any one of the above explained embodiments in place of the bundle 4X of the eleventh embodiment.

What is claimed is:

1. A device for performing non-invasive determination of a glucose concentration in the blood of a subject, said device comprising:

a light source for producing near-infrared radiation having successive wavelengths within a range of 1300 nm to 2500 nm;

light projecting means for projecting said near-infrared radiation on a skin of said subject;

light receiving means for receiving a resulting radiation emitted from the inside of said skin; and spectrum analyzing means for making a spectrum analysis of the resulting radiation and determining said glucose concentration in the blood of said subject according to the spectrum analysis, wherein said light receiving means is separated from said light projecting means by a distance in a range of 0.1 mm to 2 mm to permit selective sensing of the resulting radiation emitted from a dermis layer positioned under an epidermis layer of said skin, wherein said spectrum analyzing means determines said glucose concentration in the blood of said subject according to the spectrum analysis and a statistically-obtained correlation between glucose concentration in the dermis layer and glucose concentration in blood, wherein said light projecting means is formed with a plurality of first optical fibers, each of which is connected at a first end to said light source, and provides said near-infrared radiation from an opposite projection end, and wherein said light receiving means is formed with a plurality of second optical fibers each of which is connected at a first end to said spectrum analyzing means, and receives the resulting radiation at an opposite receiving end.

2. The device as set forth in claim 1, wherein said near-infrared radiation comprises at least one of successive wavelengths from 1400 nm to 1800 nm, and successive wavelengths from 2000 nm to 2500 nm.

3. The device as set forth in claim 1, wherein said first optical fibers make a bundle in cooperation with said second optical fibers, and the projection ends of said first optical fibers and the receiving ends of said second optical fibers are exposed on an end surface of said bundle in a pattern such that a center of each of said projection ends is separated from a center of an adjacent receiving end by said distance.

4. The device as set forth in claim 3, wherein said bundle is formed with a plurality of sub-bundles, in each of which a projection end of said first optical fiber is disposed on the end surface of said bundle at a center of a hexagonal pattern and six receiving ends of said second optical fibers are disposed at corners of said hexagonal pattern.

5. The device as set forth in claim 4, wherein at least one of said receiving ends of each of said sub-bundles is common with an adjacent sub-bundle.

6. The device as set forth in claim 4, further comprising supplemental light receiving means which is formed with a plurality of third optical fibers, wherein each of said third optical fibers is connected at a first end to said spectrum analyzing means, and selectively receives at an opposite receiving end the resulting radiation emitted from said epidermis layer, and wherein said receiving end of each of said third optical fibers is disposed on the end surface of said bundle between said projection end and one of said receiving ends in said hexagonal pattern.

7. The device as set forth in claim 3, wherein said bundle is formed with a plurality of sub-bundles, in each of which a projection end of said first optical fiber is disposed on the end surface of said bundle at a center of a rectangular pattern and four receiving ends of said second optical fibers are disposed at corners of said rectangular pattern.

8. The device as set forth in claim 3, wherein said bundle is formed with a plurality of sub-bundles, in each of which five projection ends of said first optical fibers are disposed on the end surface of said bundle at a center of a square pattern and at four corners of said square pattern, and four receiving ends of said second optical fibers are disposed on four sides of said square pattern between adjacent projection ends.

9. The device as set forth in claim 8, wherein one receiving end and two projection ends of each of said sub-bundles are common with an adjacent sub-bundle.

10. The device as set forth in claim 3, wherein said projection ends are disposed on the end surface of said bundle along a circular pattern and inside of said circular pattern, and said receiving ends are disposed along said circular pattern and outside of said circular pattern.

11. The device as set forth in claim 3, wherein said second optical fibers have at least two different diameters.

12. The device as set forth in claim 11, wherein said bundle is formed with a plurality of sub-bundles, in each of which a projection end of said first optical fiber and two receiving ends of said second optical fibers having different diameters are disposed on the end surface of said bundle in a circular pattern.

13. The device as set forth in claim 12, further comprising supplemental light receiving means which is formed with a plurality of third optical fibers, wherein each of said third optical fibers is connected at a first end to said spectrum analyzing means, and selectively receives at an opposite receiving end the resulting radiation emitted from said epidermis layer, and wherein said receiving end of each of said third optical fibers is disposed on the end surface of said bundle so as to be closer to said projection end than said receiving ends of said second optical fibers in said circular pattern.

14. The device as set forth in claim 3, further comprising a spacer for providing a predetermined interval between each of said projection ends and the adjacent receiving end.

15. The device as set forth in claim 3, wherein the center of each of said projection ends is at least separated from the center of the adjacent receiving end by a distance L expressed by the following equation:

$$L = \{\sqrt{2} \times (d1 + d2)\}/2$$

wherein d1 is a diameter of said first optical fiber, and d2 is a diameter of said second optical fiber.

16. The device as set forth in claim 3, wherein said distance is in a range of 0.2 mm to 1 mm.

17. The device as set forth in claim 1, wherein each of said first and second optical fibers has a diameter between 70 $\mu$m and 1000 $\mu$m.

18. The device as set forth in claim 1, wherein the number of said first optical fibers is equal to one half of the number of said second optical fibers.

19. The device as set forth in claim 1, further comprising supplemental light receiving means which is formed with a plurality of third optical fibers, and wherein each of said third optical fibers is connected at a first end to said spectrum analyzing means, and selectively receives at an opposite receiving end the resulting radiation emitted from said epidermis layer.

20. The device as set forth in claim 1, wherein said distance is in a range of 0.2 mm to 1 mm.

21. A device for performing non-invasive determination of a glucose concentration in the blood of a subject, said device comprising:
- a light source for producing near-infrared radiation having successive wavelengths within a range of 1300 nm to 2500 nm;
- a light projecting member which projects said near-infrared radiation on a skin of said subject;
- a light receiving member which receives a resulting radiation emitted from the inside of said skin; and
- a spectrum analyzer which makes a spectrum analysis of the resulting radiation and determines said glucose concentration in the blood of said subject according to the spectrum analysis,
    wherein said light receiving member is separated from said light projecting member by a distance in a range of 0.1 mm to 2 mm to permit selective sensing of the resulting radiation emitted from a dermis layer positioned under an epidermis layer of said skin, and said spectrum analyzer determines said glucose concentration in the blood of said subject according to the spectrum analysis and a statistically-obtained correlation between glucose concentration in the dermis layer and glucose concentration in blood
    wherein said light projecting member is formed with a plurality of first optical fibers, each of which is connected at a first end to said light source, and provides said near-infrared radiation from an opposite projection end, and
    wherein said light receiving member is formed with a plurality of second optical fibers each of which is connected at a first end to said spectrum analyzer and receives the resulting radiation at an opposite receiving end.

22. The device as set forth in claim 21, wherein said distance is in a range of 0.2 mm to 1 mm.

* * * * *